(12) United States Patent
Merino et al.

(10) Patent No.: US 9,394,233 B2
(45) Date of Patent: Jul. 19, 2016

(54) ROS-ACTIVATED COMPOUNDS AS SELECTIVE ANTI-CANCER THERAPEUTICS

(71) Applicants: University of Cincinnati, Cincinnati, OH (US); Cincinnati Children's Hospital Medical Center, Cincinnati, OH (US)

(72) Inventors: Edward J. Merino, Cincinnati, OH (US); James C. Mulloy, Cincinnati, OH (US); Guorui Li, Baltimore, MD (US); Tiffany Bell-Horwath, Cheviot, OH (US)

(73) Assignees: Cincinnati Children's Hospital Medical Center, Cincinnati, OH (US); University of Cincinnati, Cincinnati, OH (US)

( * ) Notice: Subject to any disclaimer, the term of this patent is extended or adjusted under 35 U.S.C. 154(b) by 509 days.

(21) Appl. No.: 13/782,202

(22) Filed: Mar. 1, 2013

(65) Prior Publication Data
US 2013/0230542 A1  Sep. 5, 2013

Related U.S. Application Data

(60) Provisional application No. 61/605,515, filed on Mar. 1, 2012.

(51) Int. Cl.

| | |
|---|---|
| *A61K 39/00* | (2006.01) |
| *C07C 217/20* | (2006.01) |
| *A61K 31/138* | (2006.01) |
| *C07C 321/28* | (2006.01) |
| *A61K 31/145* | (2006.01) |
| *A61K 31/167* | (2006.01) |
| *C07C 237/08* | (2006.01) |
| *C07D 295/096* | (2006.01) |
| *A61K 31/451* | (2006.01) |
| *C07C 229/42* | (2006.01) |
| *A61K 31/196* | (2006.01) |
| *A61K 31/216* | (2006.01) |
| *A61K 31/215* | (2006.01) |
| *A61K 45/06* | (2006.01) |
| *C07C 233/25* | (2006.01) |
| *C07C 217/84* | (2006.01) |
| *C07C 323/25* | (2006.01) |
| *C07C 237/04* | (2006.01) |

(52) U.S. Cl.
CPC ............ *C07C 217/20* (2013.01); *A61K 31/138* (2013.01); *A61K 31/145* (2013.01); *A61K 31/167* (2013.01); *A61K 31/196* (2013.01); *A61K 31/215* (2013.01); *A61K 31/216* (2013.01); *A61K 31/451* (2013.01); *A61K 45/06* (2013.01); *C07C 217/84* (2013.01); *C07C 229/42* (2013.01); *C07C 233/25* (2013.01); *C07C 237/04* (2013.01); *C07C 237/08* (2013.01); *C07C 321/28* (2013.01); *C07C 323/25* (2013.01); *C07D 295/096* (2013.01)

(58) Field of Classification Search
CPC .. C07C 217/20; C07C 217/84; C07C 237/04; C07C 237/08; C07C 323/25; C07C 229/42; C07C 233/25; C07C 321/28; A61K 31/167; A61K 31/145; A61K 31/451; A61K 31/216; A61K 31/196; A61K 31/138; A61K 31/215; A61K 45/06; C07D 295/096
USPC ......... 514/651, 649, 619, 331, 567, 539, 534, 514/34, 49, 46, 253.06, 346, 629; 435/375; 424/178.1, 649, 623; 564/341, 168, 564/353, 221, 354; 562/452; 560/45, 138; 546/232
See application file for complete search history.

(56) References Cited

U.S. PATENT DOCUMENTS

| | | | |
|---|---|---|---|
| 3,930,037 A * | 12/1975 | Yokoyama | .............. C09B 61/00 426/252 |
| 3,993,780 A | 11/1976 | Nakao et al. | |
| 4,772,631 A * | 9/1988 | Holloway | ............. C07C 235/02 514/539 |

(Continued)

FOREIGN PATENT DOCUMENTS

| | | |
|---|---|---|
| DE | 3410070 A1 * | 3/1985 |
| WO | WO0210146 | 2/2002 |

(Continued)

OTHER PUBLICATIONS

RN100238-34-4, corresponding to the instantly recited 4-(2-(benzyl(methyl)amino)ethoxy)phenol in claim 20.*

(Continued)

*Primary Examiner* — Jason Sims
*Assistant Examiner* — Ibrahim D Bori
(74) *Attorney, Agent, or Firm* — Dinsmore & Shohl LLP

(57) ABSTRACT

Provided are compounds according to the following Formula I:

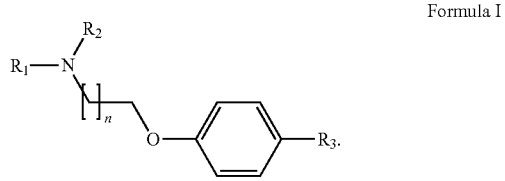

Formula I

The Formula I compounds are activated in the presence of reactive oxygen species (ROS) and are therefore selective anti-cancer therapeutics for cancers associated with elevated ROS. Also provided are methods and pharmaceutical compositions for treating cancers associated with increased ROS.

7 Claims, 11 Drawing Sheets

(56) References Cited

U.S. PATENT DOCUMENTS

2004/0072868 A1     4/2004     Collins et al.
2009/0203940 A1     8/2009     Kim et al.

FOREIGN PATENT DOCUMENTS

WO     WO2006044707 A1 *     4/2006
WO     WO2007072041     6/2007

OTHER PUBLICATIONS

Li et al, ChemMedChem, 2011, 6, 869-875.*

Blume et al (DE3410070A1, Published Mar. 10, 1986, Machine Translation).*
Li et al (ChemMedChem, 2011, 6, 869-875).*
RN100238-34-4 (available Feb. 15, 1986), corresponding to the instantly recited 4-(2-(benzyl(methyl)amino)ethoxy)phenol in claim 20.*
DE3410070 (A1), Oct. 3, 1985, Machine Translation.*
PubChem Compound CID 15651, Jul. 12, 2005; http://pubchem.ncbl.nlm.nih.gov/summary/summary.cgi?cid=15651>.
Jones et al, The Relationship Between the Constitution and the Effect of Chemical Compounds on Plant Growth Biochem 1949, 45:143-149; p. 145, Table 1, Aug. 4, 2015.
ISR/WO from corresponding Appln No. PCT/US2013/028614 dated Jul. 12, 2013.

* cited by examiner

Figure 6

| Cell Name | Compound | |
|---|---|---|
| | 9 | 25 |
| Renal Cancer | IC50 | IC50 |
| 786-0 | 1.9 | 3.5 |
| ACHN | 0.3 | 0.4 |
| CAKI-1 | 0.3 | 0.4 |
| RXF 393 | 2.1 | 2.6 |
| UO-31 | 0.4 | 1.5 |
| CNS Cancer | | |
| SF-268 | 2.2 | 3.2 |
| SF-539 | 0.6 | 2.8 |
| SNB-75 | 3.0 | 5.2 |
| U251 | 1.7 | 3.0 | a. All values in micromolar, all errors less than 25% b. Sulforhodamine B viability assay

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Lab synthesized
<220> FEATURE:
<221> NAME/KEY: misc_feature
<223> OTHER INFORMATION: Forward primer

<400> SEQUENCE: 1
ggcctcttcg ctattacgc                                             19

<210> SEQ ID NO 2
<211> LENGTH: 18
<212> TYPE: DNA
<213> ORGANISM: Artificial Sequence
<220> FEATURE:
<223> OTHER INFORMATION: Lab synthesized
<220> FEATURE:
<221> NAME/KEY: misc_feature
<223> OTHER INFORMATION: Reverse primer

<400> SEQUENCE: 2
atacgcaaac cgcctctc                                              18

<210> SEQ ID NO 3
<211> LENGTH: 12
<212> TYPE: DNA
<213> ORGANISM: Artificial Sequence
<220> FEATURE:
<223> OTHER INFORMATION: Lab synthesized

<400> SEQUENCE: 3
gcgcaattgc gc                                                    12

<210> SEQ ID NO 4
<211> LENGTH: 17
<212> TYPE: DNA
<213> ORGANISM: Artificial Sequence
<220> FEATURE:
<223> OTHER INFORMATION: Lab synthesized
<220> FEATURE:
<221> NAME/KEY: misc_feature
<223> OTHER INFORMATION: Erccl forward primer

<400> SEQUENCE: 4
cgtgctgtac ctctcgc                                               17
```

```
<210> SEQ ID NO 5
<211> LENGTH: 17
<212> TYPE: DNA
<213> ORGANISM: Artificial Sequence
<220> FEATURE:
<223> OTHER INFORMATION: Lab synthesized
<220> FEATURE:
<221> NAME/KEY: misc_feature
<223> OTHER INFORMATION: Erccl reverse primer

<400> SEQUENCE: 5
ctgaggaacg gttcctg                                                 17
```

ROS-ACTIVATED COMPOUNDS AS SELECTIVE ANTI-CANCER THERAPEUTICS

CROSS REFERENCE TO RELATED APPLICATIONS

This application claims priority to U.S. Provisional Application Ser. No. 61/605,515, filed Mar. 1, 2012, which is incorporated by reference herein in its entirety.

TECHNICAL FIELD

The presently disclosed subject matter relates to compounds and methods for treating cancer. More particularly, the presently disclosed subject matter relates to therapeutic compounds that are activated by and specifically target cancer cells associated with elevated levels of reactive oxygen species (ROS). Pharmaceutical compositions and methods of using the compounds to treat ROS-associated cancers are also described.

BACKGROUND

A challenge in the design of anti-cancer therapeutic drugs is the general toxicity of such drugs to proliferating cells, including a percentage of normal cells. A ubiquitous class of anti-cancer therapeutics includes compounds that modify, bind to, and inhibit the synthesis of DNA. This class lacks selectivity, leading to high levels of intolerable side effects stemming from the modification or interaction of DNA in non-cancerous, highly replicating cells. Such off-target effects limit tolerated doses and, hence, decreases efficacy.

Various strategies are currently under development with the goal of enhancing chemotherapy selectivity for cancer cells. For example, one strategy involves attaching therapeutic agents to active transport scaffolds such that bio-distribution of the therapeutic agent is selective for cancer cells. Other approaches involve antibody use, nanoparticles, enzymatic activation, and the like.

Many forms of cancer, and in particular ROS-associated cancers, have low survival rates, primarily due to high relapse rates. For example, in the United States, 44,600 new cases of leukemia, a ROS-associated cancer, were diagnosed in 2011, with a five-year survival rate of 57%. One of the deadliest forms of leukemia, acute myeloid leukemia (AML), accounted for 12,950 of those cases and 9,050 deaths.

A need remains for additional anti-cancer therapeutics, particularly those which target cancer cells with higher selectivity.

SUMMARY

Disclosed herein are novel anti-cancer compounds that are activated by reactive oxygen species (ROS), providing compounds that are selective for cancers associated with elevated ROS. In one embodiment, a compound according to Formula I is provided:

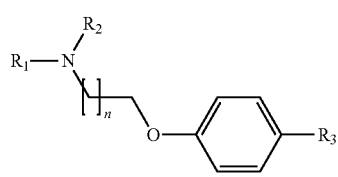

Formula I wherein: $R_1$ and $R_2$ are each independently selected from the group consisting of H, straight or branched alkyl, aryl, and aralkyl, wherein said alkyl, aryl, and aralkyl can be substituted or unsubstituted with one or more substitutions and wherein said alkyl, aryl, and aralkyl can comprise one or more heteroatoms; $R_3$ is selected from the group consisting of H, OH, $NH_2$, $NHC(O)CH_3$, piperidine, alkoxyl, $OC(O)CH_3$, and CN; and n is 1-5.

In another embodiment, a method of reducing proliferative capacity in a cell is provided, the method comprising contacting the cell with an effective amount of a compound according to Formula I.

In another embodiment, a method of treating a cancer associated with elevated ROS is provided, the method comprising administering to a subject in need thereof an effective amount of a compound according to Formula I.

In another embodiment, a pharmaceutical composition for the treatment of a cancer associated with elevated ROS is provided, the pharmaceutical composition comprising: (a) a therapeutically effective amount of a compound according to claim 1; and (b) a pharmaceutically-acceptable carrier.

These and other objects, features, embodiments, and advantages will become apparent to those of ordinary skill in the art from a reading of the following detailed description and the appended claims.

BRIEF DESCRIPTION OF THE DRAWINGS

FIG. 6 shows $IC_{50}$ (μM) results from sulforhodamine b viability assays for compounds 9 and 25 against panels of renal and CNS cancer cell lines.

DETAILED DESCRIPTION

A hallmark of many cancer cells is elevated levels of reactive oxygen species (ROS) such as superoxide, hydrogen peroxide, hydroxyl radical, and singlet oxygen. Overexpression of oncoproteins such as Ras has been linked to elevated ROS, as has the overexpression of oxidases that drive survival signals in hypoxic solid tumors. Excess ROS benefits malignant cells, increasing mutagenic DNA damage that leads to activated oncogenes and enhanced formation of adaptive advantages. Leukemia cells often have mutations that result in permanent activation of the oncogene k-Ras, a GTPase that regulates growth signals. Permanent Ras activation increases ROS levels and increases expression of proteins that allow cancer cell growth. Further, leukemic cells often have elevated NAD(P)H oxidase 2 levels compared to healthy blood cells. NAD(P)H oxidases generate ROS when performing their function. Oxidases are important in cancer progression because these enzymes have been shown to inhibit apoptosis, inactivate tumor suppressors via ROS, and enhance angiogenesis. Excess ROS further benefits malignant cells by upregulating redox-regulated growth and survival factors.

Certain ROS-associated cancer agents are currently employed in cancer therapy. For example, arsenic trioxide and doxorubicin are known to generate ROS as part of their mechanisms of action. Initial strategies to utilize elevated ROS in cancer cells focused on the inactivation of anti-oxidant glutathione. Newer ROS-associated approaches use pro-drugs that possess a hydrogen peroxide-sensitive boronic ester or agents that release toxic metabolites.

It has now been discovered that elevated ROS associated with certain cancers can be leveraged to design anti-cancer therapeutics that are activated by ROS and selectively target cancer cells, thus limiting off-target effects.

Figure 1:
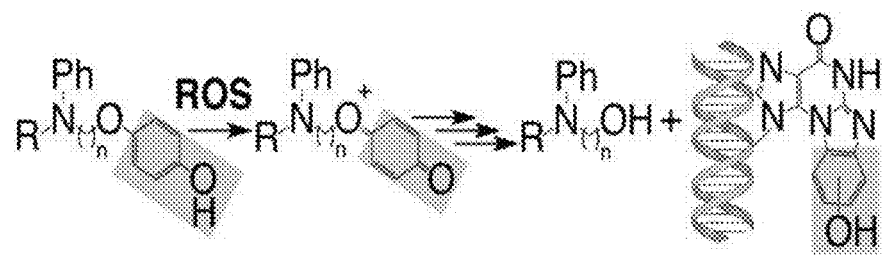
FIG. 1 shows the reaction by which an exemplary compound of the present invention is activated by ROS. In the presence of ROS, a potent electrophile is generated. The compounds disclosed herein transfer a phenol (grey shaded moiety) to DNA to predominantly form a cytotoxic hydroxy-N2,3-benzetheno-2'-deoxyguanosine adduct.

The compounds disclosed herein employ an activation strategy, whereby the compounds are locked in an inactive state until unlocked by a cancer cell-specific phenotype that converts the agent into a cytotoxic DNA modifying agent. Elevated levels of ROS convert the instant compounds into highly cytotoxic DNA-modifying agents. The activation strategy enhances the selectivity of the agents, rendering them less capable of exerting a cytotoxic mechanism of action on normal cells. FIG. 1 shows the process by which an exemplary compound of the present invention is activated by ROS. In the presence of ROS, a potent electrophile is generated, which serves as the active DNA-modifying agent. The compounds disclosed herein through a series of reactions transfer a phenol (shown in grey box) to DNA to predominantly form a cytotoxic hydroxy-N2,3-benzetheno-2'-deoxyguanosine adduct. Thus, while not desiring to be bound by theory, it is believed that the ROS-activated compounds disclosed herein induce a large, bulky phenol lesion, which requires DNA repair for cellular survival as part of their mechanism of action.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

The terms "Reactive oxygen species" or "ROS" refer to chemically reactive molecules containing oxygen. ROS include, for example, superoxide, hydrogen peroxide, hydroxyl radical, and singlet oxygen.

The term "cancer" as used herein refers to diseases caused by uncontrolled cell division and the ability of cells to metastasize, or to establish new growth in additional sites. The terms "malignant," "malignancy," "neoplasm," "tumor," and variations thereof refer to cancerous cells or groups of cancerous cells.

In certain embodiments, "cancer" refers to a cancer associated with elevated levels of ROS. Specific types of cancer associated with elevated ROS include, but are not limited to, leukemia, including acute myeloid leukemia, acute lymphoblastic leukemia, plasmacytoma, myeloma, myelogenous leukemia, acute lymphocytic leukemia, acute promyelocytic leukemia, and multiple myeloma; renal cancer; and cancers of the central nervous system.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to substituted or unsubstituted alkyl, alkoxyl, halo, hydroxyl (—OH), cyano (—CN), carboxyl, carboxyl ester, aryloxyl, alkylthio, arylthio, aralkyloxyl, aralkylthio, alkoxycarbonyl, oxo, arylamino, acyl, and cycloalkyl. There can be optionally inserted along the alkyl chain one or more heteroatoms, such as oxygen, sulfur or substituted or unsubstituted nitrogen atoms, wherein the nitrogen substituent is hydrogen, lower alkyl (also referred to herein as "alkylaminoalkyl"), or aryl. In a specific embodiment, alkyl substitutions are selected from the group consisting of alkoxyl, halo, hydroxyl (—OH), cyano (—CN), carboxyl, carboxyl ester, substituted or unsubstituted alkyl, and combinations thereof.

Thus, as used herein, the term "substituted alkyl" includes alkyl groups, as defined herein, in which one or more atoms or functional groups of the alkyl group are replaced with another atom or functional group, including for example, alkoxyl, halo, hydroxyl (—OH), cyano (—CN), carboxyl, carboxyl ester, and substituted or unsubstituted alkyl.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings. In a very specific embodiment, the aryl moiety is phenyl.

The aryl group can be optionally substituted (a "substituted aryl") with one or more aryl group substituents, which can be the same or different, wherein "aryl group substituent" includes substituted or unsubstituted alkyl, substituted or unsubstituted aryl, substituted or unsubstituted aralkyl, hydroxyl (—OH), cyano (—CN), alkoxyl, aryloxyl, aralkyloxyl, carboxyl, carboxyl ester, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkoxyl, halo, hydroxyl (—OH), cyano (—CN), carboxyl, carboxyl ester, and substituted or unsubstituted alkyl.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

As used herein, the term "aza" refers to a heterocyclic ring structure containing at least one nitrogen atom. Specific examples of aza groups include, but are not limited to, pyrrolidine, piperidine, quinuclidine, pyridine, pyrrole, indole, purine, pyridazine, pyrimidine, and pyrazine.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl."

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

The term "amino" refers to the —$NH_2$ group.

The term "carbonyl" refers to the —(C=O)— group.

The term "carboxyl" refers to the —COOH group. The term "carboxyl ester" refers to the —C(O)OR' group.

The terms "halo," "halide," or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term "cyano" refers to the —CN group.

When the term "independently selected" is used, the substituents being referred to (e.g., R groups, such as groups $R_1$ and $R_2$), can be identical or different. For example, both $R_1$ and $R_2$ can be substituted alkyls, or $R_1$ can be hydrogen and $R_2$ can be a substituted alkyl, and the like.

II. Compounds

The presently disclosed subject matter provides ROS-activated compounds according to the following Formula I:

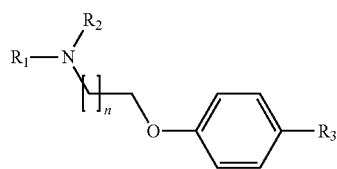

Formula I wherein:

$R_1$ and $R_2$ are each independently selected from the group consisting of H, straight or branched alkyl, aryl, and aralkyl, wherein said alkyl, aryl, and aralkyl can be substituted or unsubstituted with one or more substitutions and wherein said alkyl, aryl, and aralkyl can comprise one or more heteroatoms;

$R_3$ is selected from the group consisting of H, OH, NH$_2$, NHC(O)CH$_3$, piperidine, alkoxyl, OC(O)CH$_3$, and CN; and n is 1-5.

In certain embodiments, the alkyl, aryl, and aralkyl substitutions are selected from the group consisting of alkoxyl, halo, OH, CN, carboxyl, carboxyl ester, and substituted or unsubstituted alkyl.

In a specific embodiment, $R_1$ is H or alkyl when $R_2$ is aryl or aralkyl, and $R_2$ is H or alkyl when $R_1$ is aryl or aralkyl.

In a very specific embodiment, $R_1$ and $R_2$ are each independently selected from the group consisting of H, substituted or unsubstituted $C_1$-$C_8$ alkyl, and substituted or unsubstituted phenyl; and $R_3$ is OH. In another embodiment, n can be 1, 2, 3, 4, or 5, or any combination of ranges thereof. For example, n can be 1-2, 1-3, 1-4, 1-5, 2-3, 2-4, 2-5, 3-4, 3-5, or 4-5.

In another embodiment, presently disclosed subject matter provides ROS-activated compounds according to the following Formula II:

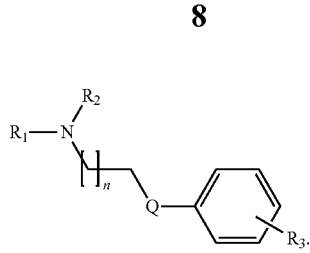

Formula II wherein:

Q is a heteroatom selected from the group consisting of O, N, or S;

$R_1$ and $R_2$ are each independently selected from the group consisting of H, straight or branched alkyl, aryl, and aralkyl, wherein said alkyl, aryl, and aralkyl can be substituted or unsubstituted with one or more substitutions and wherein said alkyl, aryl, and aralkyl can comprise one or more heteroatoms;

$R_3$ is one, two, or three substitutions at any positions on the phenyl ring, wherein the substitutions are selected from the group consisting of H, OH, NH$_2$, NHC(O)CH$_3$, piperidine, alkoxyl, OC(O)CH$_3$, alkoxyl, and CN; and n is 1-5.

In certain embodiments, the alkyl, aryl, and aralkyl substitutions are selected from the group consisting of alkoxyl, halo, OH, CN, carboxyl, carboxyl ester, and substituted or unsubstituted alkyl.

In a specific embodiment, $R_1$ is H or alkyl when $R_2$ is aryl or aralkyl, and $R_2$ is H or alkyl when $R_1$ is aryl or aralkyl.

In a very specific embodiment, $R_1$ and $R_2$ are each independently selected from the group consisting of H, substituted or unsubstituted $C_1$-$C_8$ alkyl, and substituted or unsubstituted phenyl; and $R_3$ is OH. In another embodiment, n can be 1, 2, 3, 4, or 5, or any combination of ranges thereof. For example, n can be 1-2, 1-3, 1-4, 1-5, 2-3, 2-4, 2-5, 3-4, 3-5, or 4-5.

Compounds of Formulas I or II are suitable for use as anti-cancer therapeutics for cancers associated with elevated reactive oxygen species. In a specific embodiment, the cancer is selected from the group consisting of leukemia, renal cancer, and cancers of the central nervous system. In a more specific embodiment, the leukemia is selected from the group consisting of acute myeloid leukemia, acute lymphoblastic leukemia, plasmacytoma, myeloma, myelogenous leukemia, acute lymphocytic leukemia, acute promyelocytic leukemia, and multiple myeloma.

In some embodiments, the compounds of Formulas I or II can be used to contact a cell or cell extract having elevated ROS. In some embodiments, the compound can be used to contact a tissue, tissue extract, or other biologically derived sample, such as a blood sample. In some embodiments, the compound of Formulas I or II can be used to contact a cell having elevated ROS in vivo, wherein the cell is present in a living subject, such as a mammal or bird. In some embodiments, the mammal is a human. By activating in the presence of ROS, the compound of Formulas I or II or a pharmaceutical formulation thereof can be used to modify the DNA of a cell exhibiting elevated ROS, thereby resulting in death of the cell.

III. Pharmaceutical Formulations

The compounds of Formulas I and II, the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral or intravenous administration as discussed in greater detail below. Also, the presently disclosed subject matter provides such active compounds that have been lyophilized and that can be reconstituted to form pharmaceutically acceptable formulations (including formulations pharmaceutically acceptable in humans) for administration.

The therapeutically effective dosage of any specific active compound, the use of which is within the scope of embodiments described herein, will vary somewhat from compound to compound, and subject to subject, and will depend upon the condition of the subject and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the presently disclosed methods, pharmaceutically active compounds as described herein can be administered orally as a solid or as a liquid, or can be administered intramuscularly or intravenously as a solution, suspension, or emulsion. Alternatively, the compounds or salts also can be administered intravenously or intramuscularly as a liposomal suspension.

Pharmaceutical formulations suitable for intravenous or intramuscular injection are further embodiments provided herein. The pharmaceutical formulations comprise a compound of Formulas I or II described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formulas I and II or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formulas I or II, or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. Methods of Inhibiting Cell Proliferation and Treating Cancer with Ros-Activated Compounds The presently disclosed subject matter provides methods and compositions for inhibiting cell proliferation. In particular, the presently disclosed subject matter provides methods of specifically targeting cancer cells associated with increased concentrations of reactive oxygen species (ROS). Thus, the presently disclosed subject matter provides a method of treating diseases, including cancer, which are associated with increased production of ROS.

In some embodiments, the methods for inhibiting cell proliferation or treating a cancer comprise administering to a subject in need thereof an active compound as described herein. These active compounds, as set forth above, include the compounds of Formulas I and II, their corresponding prodrugs, and pharmaceutically acceptable salts of the compounds and prodrugs. In some embodiments, the active compound is present in a pharmaceutical formulation as described hereinabove.

The presently disclosed compounds can provide therapy for a wide variety of tumors and cancers including leukemia, renal cancers, central nervous system (CNS) cancers, and other cancers associated with increased production of ROS.

An "effective amount" is defined herein in relation to the treatment of cancers is an amount that will decrease, reduce, inhibit, or otherwise abrogate the growth of a cancer cell or tumor. In some embodiments, the compound of Formulas I or II can be delivered regionally to a particular affected region or regions of the subject's body. In some embodiments, wherein such treatment is considered more suitable, the compound of Formulas I or II can be administered systemically. For example, the compound can be administered orally or intravenously.

In addition, it will be appreciated that therapeutic benefits for the treatment of cancer can be realized by combining treatment with a ROS-activated compound or other compound of the presently disclosed subject matter with one or more additional anti-cancer agents or treatments. The choice of such combinations will depend on various factors including, but not limited to, the type of disease, the age and general health of the subject, the aggressiveness of disease progression, and the ability of the subject to tolerate the agents that comprise the combination. For example, the ROS-activated compound can be combined with other agents and therapeutic regimens that are effective at reducing tumor size (e.g., radiation, surgery, hormonal treatments, and or gene therapy). Further, in some embodiments, it can be desirable to combine the ROS-activated compound with one or more agents that treat the side effects of a disease or the side effects of one of the therapeutic agents, e.g., providing the subject with an analgesic, or agents effective to stimulate the subject's own immune response (e.g., colony stimulating factor).

A variety of additional therapeutic agents, also described as "anti-neoplastic" agents or "chemotherapeutic agents" can be used in combination with one or more of the ROS-activated compounds of the presently described subject matter. Such compounds include, but are not limited to, alkylating agents, antibiotics, antimetabolites, DNA intercalators, protein synthesis inhibitors, inhibitors of DNA or RNA synthesis, DNA base analogs, topoisomerase inhibitors, anti-angiogenesis agents, telomerase inhibitors or telomeric DNA binding compounds, and P-glycoprotein inhibitors.

For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim.

Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents such as distamycin and netropsin, also can be combined with compounds of the presently disclosed subject matter in pharmaceutical compositions.

Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the ROS-activated compounds of the presently disclosed subject matter to provide a suitable cancer treatment.

Platinum-containing anti-cancer drugs such as cisplatin, carboplatin, and oxaliplatin can also be combined with the ROS-activated compounds of the presently disclosed subject matter to provide a suitable cancer treatment.

Inhibitors of P-glycoproteins, such as zosuquidar, tariquidar, and taniquidar, are also suitable anti-cancer therapeutics that can be combined with the ROS-activated compounds presently disclosed.

Additional chemotherapeutic agents suitable for combination with the ROS-activated compounds disclosed herein include gemtuzumab, all-trans retinoic acid (ATRA), and sorafenib.

In a more specific embodiment, therapeutic agents that can be used in a combination treatment with a ROS-activated compound of the presently disclosed subject matter include cytarabine, doxorubicin, cisplatin, chlorambucil, cladribine, zosuquidar, gemtuzumab, arsenic trioxide, sorafenib, and the like.

Combination treatments involving a ROS-activated compound and another therapeutic agent, such as another chemotherapeutic agent can be achieved by contacting cells with the ROS-activated compound and the other agent at the same time. Such combination treatments can be achieved by contacting the cell with a single composition or pharmacological formulation that includes both agents, or by contacting the cell with two distinct compositions or formulations, at the same time, wherein one composition includes the ROS-activated compound and the other includes the other agent.

Alternatively, treatment with the ROS-activated compound can precede or follow treatment with the other agent by intervals ranging from minutes to weeks. In embodiments where the other agent and the ROS-activated compound therapy are applied separately to the cell, one would generally ensure that a significant period of time did not expire between the time of each delivery, such that the agent and the ROS-activated compound treatment would still be able to exert an advantageously combined effect on the cell. In such instances, it is provided that one would contact the cell with both modalities within about 12-24 hours of each other and, optionally, within about 6-12 hours of each other. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations. Also, under some circumstances, more than one administration of either the ROS-activated compound or of the other agent will be desired.

In another embodiment, a ROS-activated compound of the presently disclosed subject matter or another anti-cancer compound being used in combination with the ROS-activated compound is either combined with or covalently bound to a cytotoxic agent bound to a targeting agent, such as a monoclonal antibody (e.g., a murine or humanized monoclonal antibody). It will be appreciated that the latter combination can allow the introduction of cytotoxic agents into cancer cells with greater specificity. Thus, the active form of the cytotoxic agent (i.e., the free form) will be present only in cells targeted by the antibody.

Additional cancer treatments also can be used in combination with administration of a ROS-activated compound. For example, a ROS-activated compound of the presently disclosed subject matter can be used as part of a treatment course further involving attempts to surgically remove part or all of a cancerous growth. For instance, a ROS-activated compound of the presently disclosed subject matter can be administered after surgical treatment of a subject to treat any remaining neoplastic or metastasized cells. Treatment with a ROS-activated compound of the presently disclosed subject matter also can precede surgery, in an effort to shrink the size of a tumor to reduce the amount of tissue to be excised, thereby making the surgery less invasive and traumatic.

Treating cancer with a ROS-activated compound of the presently disclosed subject matter can further include one or more treatment courses with a radiotherapeutic agent to induce DNA damage. Radiotherapeutic agents, include, for example, gamma irradiation, X-rays, UV-irradiation, microwaves, electronic emissions, radioisotopes, and the like. Therapy can be achieved by irradiating the localized tumor site with the above-described forms of radiation.

A combination therapy also can involve immunotherapy directed at tumor antigen markers that are found on the surface of tumor cells. Treatment of a cancer with a ROS-activated compound of the presently disclosed subject matter can further be combined with a gene therapy based treatment, targeted towards oncogenes and/or cell cycle controlling genes, such as p53, p16, p21, Rb, APC, DCC, NF-1, NF-2, BRCA2, FHIT, WT-1, MEN-I, MEN-II, BRCA1, VHL, FCC, MCC, ras, myc, neu, raf, erb, src, fms, jun, trk, ret, gsp, hst, bcl, and abl, which are often mutated versions of their normal cellular counterparts in cancerous tissues.

The ROS-activated compounds of the presently disclosed subject matter can be tested to measure their ability to inhibit growth of cancer cells, to induce apoptosis of the cancer cells, to reduce tumor burden, and to inhibit metastases. For example, one can measure cell growth according to the MTT assay. Growth assays as measured by the MTT assay are well known in the art. In the MTT assay, cancer cells are incubated with various concentrations of anti-cancer compound, and cell viability is determined by monitoring the formation of a colored formazan salt of the tetrazolium salt, 3-(4,5-dimethylthiazol-2-yl)-2,5-diphenyltetrazolium bromide (MTT). Other known assays for measuring cell death and or cell proliferation can also be employed.

In vivo testing can be performed using a mouse xenograft model, for example, in which MA9.3 AML cancer cells are grafted onto nude mice, in which mice treated with a compound of Formulas I or II are expected to have tumor masses that, on average, increase for a period following initial dosing, but will shrink in mass with continuing treatment. In contrast, mice treated with a control (e.g., DMSO) are expected to have tumor masses that continue to increase. Additional methods of measuring the anti-neoplastic effects of the presently disclosed compounds are described further, hereinbelow, in the Examples.

EXAMPLES

The presently disclosed subject matter will be described more fully hereinafter with reference to the accompanying Examples, in which representative embodiments are shown. The presently disclosed subject matter can, however, be embodied in different forms and should not be construed as limited to the embodiments set forth herein.

Example 1

ROS-Activated Compounds

Table 1 sets forth ROS-Activated compounds of the present invention, together with their $IC_{50}$ values corresponding to a 50% reduction in the percent of viable HeLa cells in vitro as measured via MTT assay.

TABLE 1

ROS-Activated Compounds

| Compound | | $IC_{50}$ against HeLa Cells (μM) | Formula |
|---|---|---|---|
| 1 | 4-(2-(phenylamino)ethoxy)phenol | 30 +/− 6 | I and II |

TABLE 1-continued

| | ROS-Activated Compounds | | |
|---|---|---|---|
| | Compound | IC$_{50}$ against HeLa Cells (μM) | Formula |
| 2 | 4-(2-(methyl(phenyl)amino)ethoxy)phenol | 18 +/− 3 | I and II |
| 3 | 4-(2-(ethyl(phenyl)amino)ethoxy)phenol | 23 +/− 5 | I and II |
| 4 | 4-(2-(isopropyl(phenyl)amino)ethoxy)phenol | 53 +/− 7 | I and II |
| 5 | 4-(2-((4-methoxyphenyl)amino)ethoxy)phenol | 24 +/− 1 | I and II |
| 6 | 4-(2-((4-methoxyphenyl)(methyl)amino)ethoxy)phenol | 13 +/− 5 | I and II |

TABLE 1-continued

| | ROS-Activated Compounds | | |
|---|---|---|---|
| | Compound | IC$_{50}$ against HeLa Cells (μM) | Formula |
| 7 | 4-(2-((4-bromophenyl)amino)ethoxy)phenol | 31 +/− 5 | I and II |
| 8 | 4-(2-(benzyl(methyl)amino)ethoxy)phenol | 30 +/− 1 | I and II |
| 9 | 4-(3-(methyl(phenyl)amino)propoxy)phenol | 7 +/− 2 | I and II |
| 10 | 4-(3-(ethyl(phenyl)amino)propoxy)phenol | 16 +/− 1 | I and II |
| 11 | 4-(4-(methyl(phenyl)amino)butoxy)phenol | 8 +/− 2 | I and II |
| 12 | 4-(4-(ethyl(phenyl)amino)butoxy)phenol | 14 +/− 2 | I and II |

TABLE 1-continued

| | ROS-Activated Compounds | | |
|---|---|---|---|
| | Compound | IC$_{50}$ against HeLa Cells (μM) | Formula |
| 13 | 4-(5-(methyl(phenyl)amino)pentyloxy)phenol | 9 +/− 2 | I and II |
| 14 | 4-((5-(methyl(phenyl)amino)pentyl)oxy)phenol | 13 +/− 2 | I and II |
| 15 | 4-((2-(ethyl(phenyl)amino)ethyl)thio)phenol | 46 +/− 5 | II |
| 16 | 4-((3-(methyl(phenyl)amino)propyl)thio)phenol | 44 +/− 2 | II |
| 17 | 2-(ethyl(phenyl)amino)-N-(4-hydroxyphenyl)acetamide | 108 +/− 5 | |

TABLE 1-continued

ROS-Activated Compounds

| | Compound | IC$_{50}$ against HeLa Cells (μM) | Formula |
|---|---|---|---|
| 18 | 3-(2-(ethyl(phenyl)amino)ethoxy)phenol | 44 +/− 4 | II |
| 19 | 2-(2-ethyl(phenyl)amino)ethoxy)phenol | 77 +/− 6 | II |
| 20 | N-(2-(4-aminophenoxy)ethyl)-N-ethylaniline | >125 | II |
| 21 | N-(4-(2-(ethyl(phenyl)amino)ethoxy)phenyl)acetamide | 45 +/− 5 | II |
| 22 | N-ethyl-N-(2-(4-(piperidin-1-yl)phenoxy)ethyl)aniline | >125 | II |
| 23 | N-methyl-N-(3-phenoxypropyl)aniline | >125 | II |

TABLE 1-continued

| | ROS-Activated Compounds | | |
|---|---|---|---|
| | Compound | IC$_{50}$ against HeLa Cells (μM) | Formula |
| 24 | 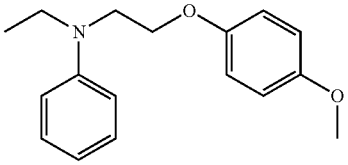 [SMILES: CCN(CCOc1ccc(OC)cc1)c1ccccc1]<br>N-ethyl-N-(2-(4-methoxyphenoxy)ethyl)aniline | >125 | II |
| 25 | 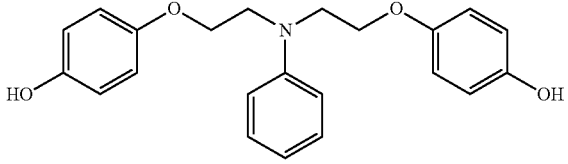 [SMILES: Oc1ccc(OCCN(CCOc2ccc(O)cc2)c2ccccc2)cc1]<br>4,4'-(2,2'-phenylazanediyl)bis(ethane-2,1-diyl)bis(oxy))diphenol | 11 +/− 2 | I and II |
| 26 | 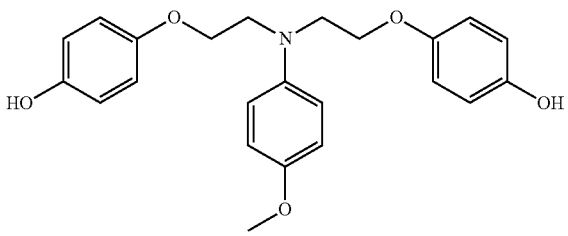 [SMILES: COc1ccc(N(CCOc2ccc(O)cc2)CCOc2ccc(O)cc2)cc1]<br>4,4'-((((4-methoxyphenyl)azanediyl)bis(ethane-2,1-diyl))bis(oxy))diphenol | 15 +/− 4 | I and II |
| 27 | 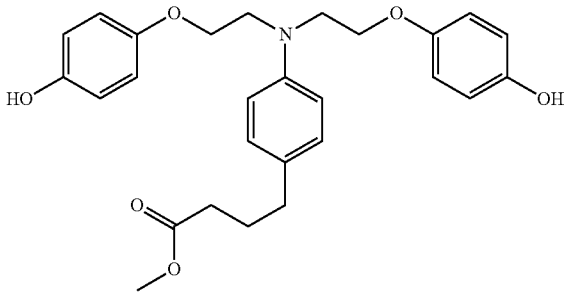 [SMILES: COC(=O)CCCc1ccc(N(CCOc2ccc(O)cc2)CCOc2ccc(O)cc2)cc1]<br>methyl 4-(4-bis(2-(4-hydroxyphenoxy)ethyl)amino)phenyl)butanoate | 77 +/− 8 | I and II |
| 28 | 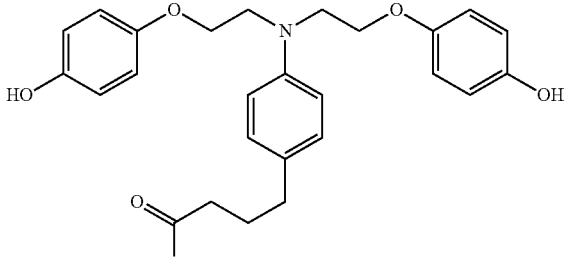<br>4-(4-(bis(2-(4-hydroxyphenoxy)ethyl)amino)phenyl)butanoic acid | 67 +/− 6 | I and II |

TABLE 1-continued

ROS-Activated Compounds

| Compound | | IC$_{50}$ against HeLa Cells (μM) | Formula |
|---|---|---|---|
| 29 | (((phenylazanediyl)bis(ethane-2,1-diyl))bis(oxy))bis(4,1-phenylene)diacetate | 12 +/− 1 | I and II |

Example 2

Synthesis of ROS-Activated Compounds

General Scheme

All synthesized compounds were purified to greater than 98% purity prior to cell testing. HeLa cell viability assays were performed using an MTT assay.

A generalized approach to compound synthesis of compounds of Formulas I or II is detailed in Scheme 1 below. Route A utilizes a substitution reaction between the amine and an iodo-alkanol. The resulting alcohol derivative is chlorinated by SOCl$_2$ and purified using automated flash silica-based chromatography. The purified chloro compound is then incubated with base, activator, and an appropriate aryl-compound. Workup, solvent evaporation, silica gel chromatography yield a final test compound. Route B begins with an appropriate Q-aryl-R$_3$ compound. This compound is treated with a 1,N-dibromoalkane. The product is then treated with a substituted amine to generate the final target compound. In another embodiment, Route C is utilizes formation of a chloro-amide compound. The target compound is formed by subsequent reduction.

General Synthetic Approaches

Route A

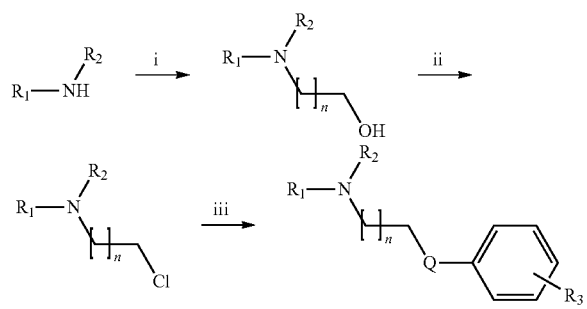

Route B

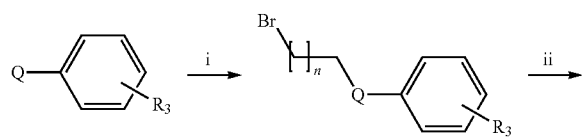

Route C

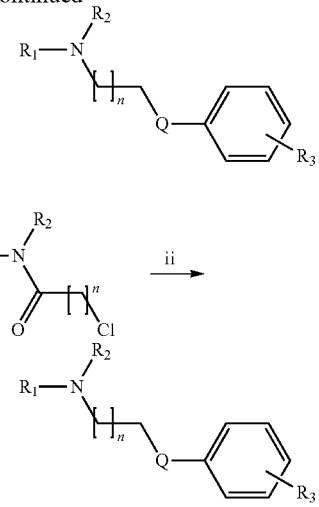

Route A. i) R$_1$R$_2$NH, iodoalkanol, KI, N,N-Diisopropylethylamine, H$_3$CCN, 60° C., overnight. ii) SOCl$_2$, dichloromethane, 25° C., 0.5 h. iii) Q-aryl-R3, K$_2$CO$_3$, KI, Argon, 80° C. Route B. i) 1,N-dibromoalkane, KOH, CH$_3$OH, reflux, 12 h. ii) R$_1$R$_2$NH, N,N-Diisopropylethylamine, H$_3$CCN, 70° C., 6 h. Route C. i) R$_1$R$_2$NH, N-chloro-alkyl acid chloride, N,N-Diisopropylethylamine, H$_3$CCN, 25° C., 0.5 h. ii) Starting material, excess LiAlH$_4$, THF, 1-5 hrs.

Due to the structural variation and exact stabilities, synthesis of specific compounds is detailed herein below. NMR ($^1$H and $^{13}$C) spectra were recorded on Bruker AMX 400 MHz spectrometer. Chemical resonances were reported in δ (ppm) units using $^{13}$C and residual $^1$H signals from deuterated solvents as references. High-resolution mass spectra (ESI) were recorded on a Micromass Q-TOF 2 (Waters, Milford, Mass.). Analytical thin layer chromatography (TLC) was performed on silica gel 60 GF254 (Merck, Whitehouse Station, N.J.). Compounds were greater than 99% pure according to HPLC.

Synthesis of Compounds

1. Synthesis of 4-(2-(phenylamino)ethoxy)phenol (1)

Synthesis of 2-chloro-N-phenylacetamide (1a)

To a solution of aniline (1 mL, 11 mmol) and CH$_2$Cl$_2$ (150 mL), pyridine (886 mL, 1 mmol) was added. Then 2-chloroacetyl chloride (872 mL, 11 mmol) was added dropwise over 10 min. After the addition was complete, the mixture was reacted at room temperature for 2 hours. The reaction was then quenched with water (100 mL), the layers were separated and the aqueous layer was extracted with CH$_2$Cl$_2$ (2×50 mL). The combined organic layer was washed water, brine, and dried over Na$_2$SO$_4$. The solvent was evaporated to give a colorless solid (1.7 g, 91% yield). The crude product was directly used for next step. $^1$H NMR (CDCl$_3$, 400 MHz) δ 8.25 (br s., 1H), 7.57 (d, J=7.6 Hz, 2H), 7.39 (t, J=7.6 Hz, 2H), 7.20 (t, J=7.4 Hz, 1H), 4.22 (s, 2H).

Synthesis of 2-(4-hydroxyphenoxy)-N-phenylacetamide (1b)

A mixture of compound 1a (338 mg, 2 mmol), K$_2$CO$_3$ (553 mg, 4 mmol), and KI (66 mg, 0.4 mmol) in DMF (50 mL) was bubbled with argon for 10 min Hydroquinone (440 mg, 4 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water and then brine and was dried over Na$_2$SO$_4$. The solvent was evaporated and the residue was purified by flash chromatography on silica gel to provide the compound (150 mg, 0.62 mmol, 31% yield) as a yellow solid. $^1$H NMR (CDCl$_3$, 400 MHz) δ 8.32 (br s, 1H), 7.60 (d, J=7.6 Hz, 2H), 7.38 (t, J=7.8 Hz, 2H), 7.18 (t, J=7.4 Hz, 1H), 6.90 (d, J=9.2 Hz, 2H), 6.84 (d, J=9.2 Hz, 2H), 5.07 (br s, 1H), 4.58 (s, 2H).

Synthesis of 4-(2-(phenylamino)ethoxy)phenol (1)

Compound 1b (1.5 g, 6.1 mmol) was dissolved in anhydrous THF (50 mL). LiAlH$_4$ (500 mg, 13 mmol) was added to the mixture under argon. The reaction mixture was heated to reflux for 4 hr. After cooling to room temperature, the reaction was carefully quenched with water (50 mL). The mixture was adjusted pH to ~7 with diluted hydrochloric acid. The mixture was then extracted with EtOAc and the combined organic layer was washed with water and then brine and dried over Na$_2$SO$_4$. The solvent was evaporated and the residue was purified by flash chromatography on silica gel to provide the product compound 1 (190 mg, 0.83 mmol, 14% yield) as a pale-yellow powder. HRMS (ESI, positive) m/z calcd. for C14H16NO2 [M+H]+: 230.1181, found: 230.1190; m/z calcd. for C14H15NO2Na [M+Na]+: 252.1001, found: 251.1061. $^1$H NMR (CDCl$_3$, 400 MHz) δ 7.25 (t, J=8.6 Hz, 2H), 6.83-6.76 (m, 5H), 6.71 (d, J=7.2 Hz, 2H), 4.12 (t, J=5.0 Hz, 2H), 3.52 (t, J=5.0 Hz, 2H).

2. Synthesis of 4-(2-(methyl(phenyl)amino)ethoxy)phenol (2)

Synthesis of 2-(methyl(phenyl)amino)ethanol (2a)

N-methylaniline (5 mls, 0.05 mol) was reacted with 2-Iodoethanol (3.599 mls, 0.05 mol) and diisopropylethylamine (8.039 mls, 0.05 mol) in ACN at 70° C. for 16 hours. The solvent was evaporated and the residue was purified by silica gel column chromatography with hexane/EtOAc to provide the compound as a yellow orange oil, 2a (4.48 g, 0.03 mol, 64.5% yield). $^1$H NMR (400 MHz, Chloroform-d) δ 7.27-7.15 (m, 2H), 6.81-6.67 (m, 3H), 3.74 (t, J=5.8 Hz, 2H), 3.42 (t, J=5.8 Hz, 2H), 2.92 (s, 3H).

Synthesis of N-(2-chloroethyl)-N-methylaniline (2b)

In a mixture of compound 2a (1.25 g, 8.3 mmol) and CH$_2$Cl$_2$ (50 mL), SOCl$_2$ (1.2 mls, 16.5 mmol) was added dropwise over 20 min. During addition the solution turned from colorless to yellow. After the addition was complete, the mixture was heated to reflux for one hour. After cooling to room temperature, the mixture was quenched carefully with cold, saturated aqueous K$_2$CO$_3$ (50 mL). The mixture was then extracted with CH$_2$Cl$_2$, and the combined organic layer was washed with brine and dried over Na$_2$SO$_4$. The solvent was evaporated and the residue was purified by silica gel column chromatography with hexane/EtOAc to provide the compound 2b (0.55 g, 3.2 mmol, 39.3% yield) as a yellow oil. HRMS (ESI, positive) m/z calcd. for C9H13ClN [M+H]+: 170.07310, found: 170.07309. $^1$H NMR (400 MHz, Chloroform-d) δ 7.24 (dd, J=8.8, 7.3 Hz, 2H), 6.73 (m, J=14.2, 7.6 Hz, 3H), 3.71-3.56 (m, 4H), 3.00 (s, 3H).

Synthesis of 4-(2-(methyl(phenyl)amino)ethoxy)phenol (2)

A mixture of compound 2b (500 mg, 2.95 mmol), K$_2$CO$_3$ (815 mg, 5.9 mmol), and KI (480 mg, 2.95 mmol) in DMF (50 mL) was bubbled with argon for 10 min Hydroquinone (649 mg, 5.9 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with CH$_2$Cl$_2$ and the combined organic layer was washed with water and then brine and was dried over Na$_2$SO$_4$. The solvent was evaporated and the residue was purified by silica gel column chromatography with hexane/EtOAc to provide compound 2 as a white solid (143 mg, 0.59 mmol, 20% yield). HRMS (ESI, positive) m/z calcd. for C15H18NO2 [M+H]+: 244.13321, found: 244.13323. $^1$H NMR (400 MHz, Chloroform-d) δ 7.29 (ddd, J=7.3, 5.6, 2.0 Hz, 2H), 6.84-6.72 (m, 7H), 4.98 (broad s, 1H), 4.11 (t, J=6.1 Hz, 2H), 3.76 (t, J=6.1 Hz, 2H), 3.08 (s, 3H).

3. Synthesis of 4-(2-(ethyl(phenyl)amino)ethoxy)phenol (3)

Synthesis of N-(2-chloroethyl)-N-ethylaniline (3a)

2-(N-ethyl-N-phenylamino)ethanol (10 g, 60 mmol) in CH$_2$Cl$_2$ (150 mL) was reacted with SOCl$_2$ (8.8 mL, 121 mmol). The mixture was heated to reflux for one hour and quenched. The solvent was evaporated and the residue was purified by silica gel column chromatography to provide intermediate 3a (5.54 g, 30 mmol, 50%) as a yellow oil. $^1$H NMR (CDCl$_3$, 400 MHz) δ 7.28 (m, 2H), 6.74 (m, 3H), 3.65 (m, 4H), 3.46 (q, J=7.2 Hz, 2H), 1.22 (t, J=7.2 Hz, 3H); HRMS (ESI, positive) m/z calcd. for C10H15ClN [M+H]+: 184.0893, found: 184.0836.

Synthesis of 4-(2-(ethyl(phenyl)amino)ethoxy)phenol (3)

A mixture of compound 3a (500 mg, 2.7 mmol), K$_2$CO$_3$ (750 mg, 5.4 mmol), and KI (90 mg, 0.54 mmol) in DMF (50 mL) was bubbled with argon for 10 min Hydroquinone (600 mg, 5.4 mmol) was added to the mixture under argon. The reaction mixture was heated and stirred at 80° C. for 6 hr. The reaction was quenched and the solvent evaporated and purified by silica gel column chromatography to provide compound 3 (400 mg, 1.55 mmol, 57% yield) as a brown oil. $^1$H NMR (DMSO-d6, 400 MHz) δ 8.92 (s, 1H), 7.14 (m, 2H), 6.75-6.64 (m, 6H), 6.57 (m, 1H), 3.98 (t, J=5.8 Hz, 2H), 3.62

(t, J=5.8 Hz, 2H), 3.41 (q, J=7 Hz, 2H), 1.09 (t, J=7 Hz, 3H). HRMS (ESI, positive) m/z calcd. for C16H20NO2 [M+H]+: 258.1494, found: 258.1436.

4. Synthesis of 4-(2-(isopropyl(phenyl)amino)ethoxy)phenol (4)

Synthesis of N-isopropylaniline (4a)

A mixture of aniline (0.46 mls, 5 mmol) and cesium hydroxide (0.61 mls, 15 mmol) was stirred at 25° C. for 30 mins in DMF (25 mls). 2-iodopropane (2.5 mls, 25 mmol) was added dropwise over 5 mins, the reaction was heated to 30° C. and stirred for 16 hours. The solvent was evaporated and the residue was quenched with 100 mL water. The mixture was adjusted pH to ~7 with diluted hydrochloric acid. The mixture was then extracted with $CH_2Cl_2$ and the combined organic layer was washed with water and then brine and was dried over $Na_2SO_4$. The solvent was evaporated and the residue was purified by silica gel column chromatography with hexane/EtOAc to provide the intermediate 4a (55 mg, 4 mmol, 81.4% yield) as an orange oil. $^1$H NMR (400 MHz, $CDCl_3$) δ 7.11-7.02 (t, J=7.9 Hz, 2H), 6.63-6.54 (t, J=7.3 Hz, 2H), 6.54-6.45 (d, J=7.8 Hz, 1H), 3.60-3.45 (hept, J=6.3 Hz, 1H), 3.41-3.25 (s, 1H), 1.14-1.06 (d, J=6.3 Hz, 6H).

Synthesis of 2-(isopropyl(phenyl)amino)ethanol (4b)

Compound 4a (617 mg, 4.6 mmol) was reacted with 2-Iodoethanol (0.54 mls, 6.9 mmol) and diisopropylethylamine (1.2 mls, 6.9 mmol) in ACN (20 mls) at 30° C. for 48 hours. The solvent was evaporated and the residue was purified by silica gel column chromatography with hexane and EtOAc to provide the intermediate 4b (483 mg, 2.7 mmol, 59% yield) as a light brown oil. HRMS (ESI, positive) m/z calcd. for C11H18N1O1 [M+H]+: 180.13829, found: 180.13829. $^1$H NMR (400 MHz, $CDCl_3$) δ 7.28-7.19 (t, J=8.0 Hz, 2H), 6.92-6.85 (d, J=8.2 Hz, 2H), 6.83-6.75 (t, J=7.3 Hz, 1H), 4.03-3.88 (hept, J=6.6 Hz, 1H), 3.70-3.62 (t, J=6.2 Hz, 2H), 3.34-3.24 (m, 2H), 1.19-1.12 (d, J=6.6 Hz, 6H).

Synthesis of N-(2-chloroethyl)-N-isopropylaniline (4c)

In a mixture of compound 4b (483 mg, 2.7 mmol) and $CH_2Cl_2$ (50 mL), $SOCl_2$ (0.24 ml, 3.2 mmol) was added dropwise over 20 min. After the addition was complete, the mixture was heated to reflux for one hour. After cooling to room temperature, the mixture was quenched carefully with cold, saturated aqueous $K_2CO_3$ (100 mL). The mixture was then extracted with $CH_2Cl_2$, and the combined organic layer was washed with saturated aqueous $K_2CO_3$, washed with brine, and dried over $Na_2SO_4$. The solvent was evaporated and the residue was purified by silica gel column chromatography with hexane/EtOAc (8/1) to provide the intermediate 4c (170 mg, 0.86 mmol, 31.8% yield) as a yellow brown oil. $^1$H NMR (400 MHz, $CDCl_3$) δ 7.35-7.26 (m, 2H), 6.86-6.76 (m, 3H), 4.19-4.04 (hept, J=6.5 Hz, 1H), 3.65-3.50 (td, J=12.6, 7.3 Hz, 4H), 1.29-1.22 (d, J=6.6 Hz, 6H).

Synthesis of 4-(2-(isopropyl(phenyl)amino)ethoxy)phenol (4)

A mixture of compound 4c (400 mg, 2 mmol), $K_2CO_3$ (558 mg, 4 mmol), and KI (720 mg, 4 mmol) in DMF (50 mL) was bubbled with argon for 10 min Hydroquinone (440 mg, 4 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with $CH_2Cl_2$ and the combined organic layer was washed with water and then brine and was dried over $Na_2SO_4$. The solvent was evaporated and the residue was purified by silica gel column chromatography to provide compound 4 (210 mg, 0.77 mmol, 38.3% yield) as a brown oil. HRMS (ESI, positive) m/z calcd. for C17H22N1O2 [M+H]+: 272.16451, found: 272.16455. $^1$H NMR (400 MHz, $CDCl_3$) δ 7.16-7.05 (m, 2H), 6.75-6.56 (m, 7H), 4.08-3.83 (m, 4H), 3.50-3.42 (t, J=7.1 Hz, 1H), 1.19-1.06 (m, 6H).

5. Synthesis of 4-(2-((4-methoxyphenyl)amino)ethoxy)phenol (5)

Synthesis of 4-(2-bromoethoxy)phenol (5a)

To a solution of hydroquinone (1.0 g, 9 mmol) in MeOH (15 mL), KOH (1.02 g, 9 mmol) was added and stirred at room temperature for 30 minutes under argon. 1,2-dibromoethane (0.98 mL, 11.3 mmol) was added dropwise over 10 min. After the addition was complete, the mixture was refluxed for 12 hours. The reaction mixture was concentrated and was then quenched with water (50 mL) and the aqueous layer was extracted with EtOAc (2×25 mL). The combined organic layer was washed with water, brine, and dried over $Na_2SO_4$. The solvent was evaporated to give a colorless oil, which was purified by column chromatography to isolate the intermediate 5a as a white solid (0.39 g, 1.79 mmol, 20% yield). $^1$H NMR ($CDCl_3$, 400 MHz) δ 6.78-6.85 (m, 4H), 4.53 (s, 1H), 4.26 (t, J=6.4 Hz, 2H), 3.63 (t, J=6.4 Hz, 2H).

Synthesis of 4-(2-((4-methoxyphenyl)amino)ethoxy) phenol (5)

4-methoxy-aniline (124 mg, 1.0 mmol) and compound 5a (200 mg, 0.92 mmol) were reacted in acetonitrile (10.0 mL) for 30 mins and diisopropylethylamine was added (0.28 mL, 2.0 mmol) dropwise. After the addition was complete, the reaction was stirred at 60° C. for 12 hours. The reaction mixture was concentrated, purified by column chromatography to isolate the compound 5 as a colorless oil (45 mg, 0.17 mmol, 19% yield). MS (ESI, positive) m/z calcd. for C15H18NO3 [M+H]+: 260.13, found: 259.94. $^1$H NMR ($CDCl_3$, 400 MHz) δ 6.66-6.84 (m, 8H), 4.45 (bs, 1H), 4.12 (t, J=5.2 Hz, 2H), 3.89 (bs, 1H), 3.77 (s, 3H), 3.47 (t, J=5.2 Hz, 2H).

6. Synthesis of 4-(2-((4-methoxyphenyl)(methyl)amino)ethoxy)phenol (6)

Synthesis of 4-methoxy-N-methylaniline (6a)

To a solution of 4-methoxy-aniline (0.65 g, 5.28 mmol) and iodomethane (0.33 mL, 5.28 mmol) in Acetonitrile (10.0 mL), diisopropylethylamine was added (1.50 mL, 10.56 mmol) dropwise. After the addition was complete, the reaction was stirred at 60° C. for 12 hours. The reaction mixture was concentrated and the crude product 6a was used directly for the next step.

Synthesis of 4-(2-((4-methoxyphenyl)(methyl)amino)ethoxy)phenol (6)

Compound 6a (0.20 g, 1.46 mmol) and compound 5a (0.32 g, 1.46 mmol) were stirred in acetonitrile (10.0 mL) for 30 mins and then diisopropylethylamine was added dropwise (0.40 mL, 2.92 mmol). The reaction was then stirred at 60° C. for 12 hours and monitored by TLC. The reaction mixture was concentrated, purified by column chromatography to isolate the compound 6 as a colorless oil (0.10 g, 0.36 mmol, 25% yield). MS (ESI, positive) m/z calcd. for C16H20NO3 [M+H]+: 274.14, found: 273.96. $^1$H NMR (CDCl$_3$, 400 MHz) δ 6.86 (d, J=8 Hz, 2H), 6.70-6.78 (m, 6H), 4.06 (t, J=5.6 Hz, 2H), 3.78 (s, 3H), 3.64 (t, J=5.6 Hz, 2H), 2.98 (s, 3H).

7. Synthesis of 4-(2-((4-bromophenyl)amino)ethoxy)phenol (7)

Synthesis of N-(4-bromophenyl)-2-chloroacetamide (7a)

4-bromoaniline (1.72 g, 10 mmol) was dissolved in 50 mL dichloromethane. Pyridine (cat.) was added and then 2-chloroacetyl chloride (800 uL, 10 mmol) was added dropwise. The reaction was stirred at room temperature for 1 hr. The reaction was quenched with water and the aqueous layer was extracted with dichloromethane (2×25 mL). The combined organic layer was washed with water, then brine, and dried over Na$_2$SO$_4$. The solvent was evaporated to give the intermediate 7a (1.03 g, 4 mmol, 42% yield). $^1$H NMR (400 MHz, Chloroform-d) δ 8.24 (broad s, 1H), 7.54-7.44 (m, 4H), 4.21 (s, 2H).

Synthesis of N-(4-bromophenyl)-2-(4-hydroxyphenoxy)acetamide (7b)

A mixture of compound 7a (496 mg, 2 mmol), K$_2$CO$_3$ (553 mg, 4 mmol), and KI (66 mg, 0.4 mmol) in DMF (50 mL) was bubbled with argon for 10 min Hydroquinone (440 mg, 4 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water, then brine, and dried over Na$_2$SO$_4$. The solvent was evaporated and the residue was purified by silica gel column chromatography with hexane/EtOAc (3:1) to provide the intermediate 7b (100 mg, 0.3 mmol, 16% yield). $^1$H NMR (400 MHz, Chloroform-d) δ 8.30 (broad s, 1H), 7.56-7.46 (m, 4H), 6.94-6.87 (m, 2H), 6.87-6.80 (m, 2H), 4.57 (s, 2H).

Synthesis of 4-(2-((4-bromophenyl)amino)ethoxy)phenol (7)

Compound 7b (80 mg, 0.25 mmol) was dissolved in THF (5 ml). LiAlH4 (30 mg, 0.5 mmol) was added portionwise and the reaction was refluxed for 6 hrs. The reaction was quenched slowly with water, 10% sodium hydroxide, and then water again. The aqueous layer was extracted with EtOAc (2×50 mL). The organic was concentrated to yield compound 7 (10 mg, 0.03 mmol, 13% yield). $^1$H NMR (CDCl$_3$, 400 MHz) δ 7.29 (m, 2H), 6.80 (q, 4H), 6.56 (d, 2H), 4.81 (broad s, 1H), 4.13 (t, 2H), 3.47 (t, 2H); HRMS (ESI, positive) m/z calcd. for C14H14BrNO2 [M+H]+: 308.0286, found: 308.0261.

8. Synthesis of 4-(2-(benzyl(methyl)amino)ethoxy)phenol (8)

Synthesis of 4-(2-bromoethoxy)phenol (8a)

To a solution of hydroquinone (1.0 g, 9 mmol) in MeOH (15 mL), KOH (1.02 g, 9 mmol) was added and stirred at room temperature for 30 minutes under argon. 1,2-dibromoethane (0.98 mL, 11.3 mmol) was added dropwise over 10 min After the addition was complete, the mixture was refluxed for 12 hours. The reaction mixture was concentrated and was then quenched with water (50 mL) and the aqueous layer was extracted with EtOAc (2×25 mL). The combined organic layer was washed with water, then brine, and dried over Na$_2$SO$_4$. The solvent was evaporated to give a colorless oil, which was purified by column chromatography to isolate the intermediate 8a as a white solid (0.39 g, 1.79 mmol, 20% yield). $^1$H NMR (CDCl$_3$, 400 MHz) δ 6.78-6.85 (m, 4H), 4.53 (s, 1H), 4.26 (t, J=6.4 Hz, 2H), 3.63 (t, J=6.4 Hz, 2H).

Synthesis of 4-(2-(benzyl(methyl)amino)ethoxy)phenol (8)

Compound 8a (0.25 g, 1.15 mmol) and N-methyl-1-phenylmethanamine (0.18 g, 1.38 mmol) were stirred in acetonitrile (12.0 mL) for 20 mins before diisopropylethylamine was added (0.40 mL, 2.30 mmol) dropwise. After the addition was complete, the reaction was stirred at 60° C. for 12 hours and monitored by TLC. The reaction mixture was concentrated, purified by column chromatography to isolate the compound 8 as a brownish oil (0.20 g, 0.77 mmol, 67% yield). MS (ESI, positive) m/z calcd. for C16H20NO2 [M+H]+: 258.15, found: 257.98. $^1$H NMR (CDCl$_3$, 400 MHz) δ 7.30-7.37 (m, 4H), 6.74-6.82 (m, 5H), 4.05 (t, J=6 Hz, 2H), 3.78 (s, 1H), 3.645 (s, 2H), 2.83 (t, J=6.0 Hz, 2H).

9. Synthesis of 4-(3-(methyl(phenyl)amino)propoxy)phenol (9)

Synthesis of N-(3-bromopropyl)-N-methylaniline (9a)

N-methylaniline (1.01 mL, 9.33 mmol) was reacted with 1,3-dibromopropane (0.947 mL, 9.33 mmol) and diisopropylethylamine (2.55 mL, 18.66 mmol) in ACN at 70° C. for 12 hours. The solvent was evaporated and the residue was purified by silica gel column chromatography to provide the intermediate 9a as a yellow oil (0.80 g, 3.52 mmol, 37% yield). HRMS (ESI, positive) m/z calcd. for C10H15NBr [M+H]+: 228.03824, found: 228.03824. $^1$H NMR (CDCl$_3$, 400 MHz) δ 7.67 (t, J=8.4 Hz, 2H), 6.71 (d, J=8.0 Hz, 2H), 6.617 (t, J=7.2 Hz, 1H), 3.562 (t, J=6.8 Hz, 2H), 3.431 (t, J=7.2 Hz, 2H), 2.878 (s, 3H), 2.072 (m, 2H).

Synthesis of 4-(3-(methyl(phenyl)amino)propoxy)phenol (9)

A mixture of compound 9a (500 mg, 2.7 mmol), K$_2$CO$_3$ (740 mg, 5.4 mmol), and KI (445 mg, 2.7 mmol) in DMF (50 mL) was bubbled with argon for 10 min Hydroquinone (589 mg, 5.4 mmol) was added to the mixture under argon. The reaction mixture was heated and stirred at 80° C. for 6 hours. After cooling to room temperature, the solvent was evaporated and the residue was quenched with 100 mLs water. The mixture was adjusted pH to ~7 with diluted hydrochloric acid. The mixture was then extracted with CH$_2$Cl$_2$ and the combined organic layer was washed with water and then brine and was dried over Na$_2$SO$_4$. The solvent was evaporated and the residue was purified by silica gel column chromatography with hexane/EtOAc to provide the compound 9 (170 mg, 0.66 mmol, 24% yield) as a white solid. HRMS (ESI, positive) m/z calcd. for C$_{16}$H$_{20}$NO$_2$ [M+H]+: 258.14886, found: 258.14888. $^1$H NMR (400 MHz, Chloroform-d) δ 7.36-7.27

(m, 2H), 6.94-6.70 (m, 7H), 5.94 (broad s, 1H), 4.00 (t, J=5.9 Hz, 2H), 3.60 (t, J=7.0 Hz, 2H), 3.01 (s, 3H), 2.09 (p, J=6.2 Hz, 2H).

10. Synthesis of 4-(3-(ethyl(phenyl)amino)propoxy)phenol (10)

Synthesis of 4-(3-bromopropoxy)phenol (10a)

To a solution of hydroquinone (3.0 g, 27 mmol) in MeOH (30 mL), KOH (1.5 g, 27 mmol) was added. Then, 1,3-dibromopropane (3.3 mL, 32 mmol) was added dropwise over 10 minutes. After the addition was complete, the mixture was refluxed for 12 hours at 70° C. The reaction mixture was concentrated and quenched with water (100 mL), and then the aqueous layer was extracted with EtOAc (2×50 mL). The combined organic layer was with washed water, thetn brine, and dried over $Na_2SO_4$. The solvent was evaporated and the product was purified by column chromatography to isolate the intermediate 10a (1.46 g, 6.31 mmol, 23% yield) as a pinkish solid. $^1$H NMR ($CDCl_3$, 400 MHz) δ 6.81 (m, 4H), 5.93 (broad s, 1H), 4.06 (t, 2H), 3.61 (t, 2H), 2.30 (m, 2H).

Synthesis of 4-(3-(ethyl(phenyl)amino)propoxy)phenol (10)

Compound 10a (500 mg, 2.2 mmol) and N-ethylaniline (1 g, 5.5 mmol) were reacted in acetonitrile for 30 mins before diisopropylethylamine (284 mg, 2.2 mmol) was added dropwise. The reaction mixture was then heated and stirred at 70° C. for 12 hours. After cooling to room temperature, the solvent was evaporated and the residue was purified by silica gel column chromatography to provide the compound 10 (170 mg, 0.66 mmol, 24% yield) as a pale yellow solid. MS (ESI, positive) m/z calcd. for C17H21NO2 [M+H]+: 272.16, found: 272.00. $^1$H NMR (400 MHz, Chloroform-d) δ 7.25 (d, J=7.8 Hz, 2H), 6.88-6.66 (m, 7H), 3.99 (t, J=5.8 Hz, 2H), 3.53 (t, J=7.1 Hz, 2H), 3.41 (q, J=7.2 Hz, 2H), 2.08 (q, J=6.7 Hz, 2H), 1.19 (t, J=7.1 Hz, 3H).

11. Synthesis of 4-(4-(methyl(phenyl)amino)butoxy)phenol (11)

Synthesis of 4-(4-bromobutoxy)phenol (11a)

To a solution of hydroquinone (2.0 g, 18.16 mmol) in MeOH (20 mL), KOH (1.02 g, 18.2 mmol) was added and stirred at room temperature for 30 minutes under argon. 1,4-dibromobutane (2.7 mL, 22.7 mmol) was added dropwise over 10 min. After the addition was complete, the mixture was refluxed for 12 hours. The reaction mixture was concentrated and was then quenched with water (50 mL) and the aqueous layer was extracted with EtOAc (2×25 mL). The combined organic layer was washed with water, then brine, and dried over $Na_2SO_4$. The solvent was evaporated to give a colorless oil, which was purified by column chromatography to isolate the intermediate 11a as a white solid (0.80 g, 3.26 mmol, 18% yield). $^1$H NMR ($CDCl_3$, 400 MHz) δ 6.78 (s, 4H), 4.53 (s, 1H), 3.95 (t, J=6 Hz, 2H), 3.52 (t, J=6.8 Hz, 2H), 1.86-2.15 (m, 4H).

Synthesis of 4-(4-(methyl(phenyl)amino)butoxy)phenol (11)

Compound 11a (0.20 g, 0.816 mmol) and compound N-methylaniline (0.176 mL, 1.63 mmol) were stirred in acetonitrile (10 mL) for 30 mins and then diisopropylethylamine (0.33 mL, 2.44 mmol) was added dropwise. The reaction was then stirred at 60° C. for 12 hours and monitored by TLC. The reaction mixture was concentrated and treated with formic acid to facilitate purification by column chromatography to isolate compound 11 as a colorless oil (0.12 g, 0.36 mmol, 46% yield). MS (ESI, positive) m/z calcd. for C17H22NO2 [M+H]+: 272.16451, found: 272.16452. $^1$H NMR ($CDCl_3$, 400 MHz) δ 7.29 (t, J=7.2 Hz, 2H), 6.77-6.83 (m, 7H), 6.10 (bs, 1H), 3.92 (t, J=5.2 Hz, 2H), 3.41 (t, J=7.2 Hz, 2H), 2.97 (s, 3H), 1.70-1.81 (m, 4H).

12. Synthesis of 4-(4-(ethyl(phenyl)amino)butoxy)phenol (12)

Synthesis of 4-(4-bromobutoxy)phenol (12a)

To a solution of hydroquinone (2.0 g, 18.2 mmol) in MeOH (20 mL), KOH (1.0 g, 18.2 mmol) was added. Then, 1,4-dibromobutane (2.7 mL, 22.7 mmol) was added dropwise over 10 min. After the addition was complete, the mixture was refluxed for 12 hours at 70° C. The reaction mixture was concentrated and quenched with water (100 mL), and then the aqueous layer was extracted with EtOAc (2×50 mL). The combined organic layer was washed with water, then brine, and dried over $Na_2SO_4$. The solvent was evaporated to give a colorless oil, which was purified by column chromatography to isolate the intermediate 12a (0.8 g, 3.26 mmol, 18% yield). $^1$H NMR ($CDCl_3$, 400 MHz) δ 6.78 (s, 4H), 4.53 (s, 1H), 3.95 (t, J=6 Hz, 2H), 3.52 (t, J=6.8 Hz, 2H), 1.86-2.15 (m, 4H).

Synthesis of 4-(4-(ethyl(phenyl)amino)butoxy)phenol (12)

To a solution of compound 12a (250 mg, 1.02 mmol) and N-ethylaniline (0.24 mL, 2.04 mmol) in acetonitrile (5.0 mL), diisopropylethylamine (0.42 mL, 3.05 mmol) was added dropwise. After the addition was complete, the reaction was stirred at 60° C. for 12 hours. The reaction mixture was concentrated and purified by column chromatography to isolate the compound 12 as a colorless oil (20 mg, 0.07 mmol, 12% yield). MS (ESI, positive) m/z calcd. for C18H24NO2 [M+H]+: 286.18, found: 286.18. $^1$H NMR (400 MHz, Chloroform-d) δ 7.23 (t, J=8 Hz, 1H), 6.65-6.81 (m, 8H), 4.71 (bs, 1H), 3.95 (t, J=5.2 Hz, 2H), 3.33-3.52 (m, 4H), 1.27-1.33 (m, 4H), 1.17 (t, J=6.8 Hz, 3H).

13. Synthesis of 4-(5-(methyl(phenyl)amino)pentyloxy)phenol (13)

Synthesis of 4-(5-bromopentyloxy)phenol (13a)

To a solution of hydroquinone (2.0 g, 18.2 mmol) in MeOH (10 mL), KOH (1.02 g, 18.2 mmol) was added. Then 1,5-dibromopentane (3.1 mL, 22.7 mmol) was added dropwise over 10 min and the mixture was refluxed for 12 hours. The reaction mixture was concentrated, quenched with water (100 mL), and the aqueous layer was extracted with EtOAc (2×50 mL). The combined organic layer was washed water, brine, and dried over $Na_2SO_4$. The compound was purified by column chromatography to isolate intermediate 13a as a colorless oil (0.94 g, 3.26 mmol, 20% yield). $^1$H NMR ($CDCl_3$, 400 MHz) δ 6.76-6.84 (m, 4H), 4.50 (s, 1H), 3.93 (t, J=6.4 Hz, 2H), 3.46 (t, J=6.4 Hz, 2H), 1.92-1.96 (m, 2H), 1.77-1.84 (m, 2H), 1.60-1.67 (m, 2H).

Synthesis of 4-(5-(methyl(phenyl)amino)pentyloxy)phenol (13)

Compound 13a (0.15 g, 0.58 mmol) and compound N-methylaniline (0.07 mL, 0.64 mmol) were stirred in acetonitrile (5 mL) for 30 mins and then diisopropylethylamine (0.24 mL, 1.74 mmol) was added dropwise. The reaction was then stirred at 60° C. for 12 hours and monitored by TLC. The reaction mixture was concentrated and purified by column chromatography to isolate the compound 13 as a colorless oil (0.05 g, 0.36 mmol, 30% yield). MS (ESI, positive) m/z calcd. for C18H24NO2 [M+H]+: 286.18, found: 285.95. $^1$H NMR (CDCl$_3$, 400 MHz) δ 7.25 (t, J=8.8 Hz, 2H), 6.70-6.85 (m, 7H), 4.72 (s, 1H), 3.93 (t, J=6.4 Hz, 2H), 3.36 (t, J=7.6 Hz, 2H), 2.95 (s, 3H), 1.85-1.78 (m, 2H), 1.63-1.71 (m, 2H), 1.47-1.55 (m, 2H).

14. Synthesis of 4-(5-(methyl(phenyl)amino)pentyl) oxy)phenol (14)

Synthesis of 4-((5-bromopentyl)oxy)phenol (14a)

To a solution of hydroquinone (2.0 g, 18.2 mmol) in MeOH (10 mL), KOH (1.02 g, 18.2 mmol) was added. Then, 1,5-dibromopentane (3.09 mL, 22.7 mmol) was added dropwise over 10 min. After the addition was complete, the mixture was refluxed for 12 hours at 70° C. The reaction mixture was concentrated and quenched with water (100 mL), and then the aqueous layer was extracted with EtOAc (2×50 mL). The combined organic layer was washed with water, then brine, and dried over Na$_2$SO$_4$. The solvent was evaporated to give a colorless oil, which was purified by column chromatography to isolate intermediate 14a (0.94 g, 3.62 mmol, 20% yield). $^1$H NMR (CDCl$_3$, 400 MHz) δ 6.76-6.84 (m, 4H), 4.50 (s, 1H), 3.93 (t, J=6.4 Hz, 2H), 3.46 (t, J=6.4 Hz, 2H), 1.92-1.96 (m, 2H), 1.77-1.84 (m, 2H), 1.60-1.67 (m, 2H).

Synthesis of 4-((5-(methyl(phenyl)amino)pentyl) oxy)phenol (14)

To a solution of compound 14a (150 mg, 0.57 mmol) and N-ethylaniline (0.07 mL, 0.63 mmol) in acetonitrile (5.0 mL) diisopropylethylamine (0.24 mL, 1.73 mmol) was added dropwise. After the addition was complete the reaction was stirred at 60° C. for 12 hours. The reaction mixture was concentrated, purified by column chromatography to isolate the required compound 14 as a colorless oil (20 mg, 0.07 mmol, 12% yield). MS (ESI, positive) m/z calcd. for C18H24NO2 [M+H]+: 286.18, found: 285.95. $^1$H NMR (CDCl$_3$, 400 MHz) δ 7.28 (t, J=8.8 Hz, 2H), 6.70-6.85 (m, 7H), 4.72 (s, 1H), 3.93 (t, J=6.4 Hz, 2H), 3.36 (t, J=7.6 Hz, 2H), 2.95 (s, 3H), 1.85-1.78 (m, 2H), 1.65-1.71 (m, 2H), 1.47-1.55 (m, 2H).

15. Synthesis of 4-((2-(ethyl(phenyl)amino)ethyl) thio)phenol (15)

Synthesis of N-(2-chloroethyl)-N-ethylaniline (15a)

2-(N-ethyl-N-phenylamino)ethanol (10 g, 60 mmol) in CH$_2$Cl$_2$ (150 mL) was reacted with SOCl$_2$ (8.8 mL, 121 mmol). The mixture was heated to reflux for one hour and quenched. The solvent was evaporated and the residue was purified by silica gel column chromatography to provide intermediate 15a (5.54 g, 30 mmol, 50%) as a yellow oil. $^1$H NMR (CDCl$_3$, 400 MHz) δ 7.28 (m, 2H), 6.74 (m, 3H), 3.65 (m, 4H), 3.46 (q, J=7.2 Hz, 2H), 1.22 (t, J=7.2 Hz, 3H); HRMS (ESI, positive) m/z calcd. for C10H15ClN [M+H]+: 184.0893, found: 184.0836.

Synthesis of 4-((2-(ethyl(phenyl)amino)ethyl)thio) phenol (15)

Compound 15a (0.25 g, 1.36 mmol) and 4-mercaptophenol (0.14 mL, 1.36 mmol) were stirred in acetonitrile (10.0 mL) for 30 minutes before diisopropylethylamine (0.37 mL, 2.72 mmol) was added dropwise. The reaction was stirred at 60° C. for 12 hours. The reaction mixture was concentrated and purified by column chromatography to isolate intermediate 15a as a colorless oil (0.15 g, 0.55 mmol, 40% yield). MS (ESI, positive) m/z calcd. for C16H20NOS [M+H]+: 274.13, found: 273.96. $^1$H NMR (CDCl$_3$, 400 MHz) δ 7.39 (d, J=8.4 Hz, 2H), 7.18 (t, J=8.0 Hz, 2H), 6.83 (d, J=8.8 Hz, 2H), 6.66 (t, J=7.2 Hz, 1H), 6.54 (d, J=8.0 Hz, 2H), 4.92 (broad s, 1H), 3.46 (t, J=8.0 Hz, 2H), 3.34 (q, J=6.8 Hz, 2H), 2.97 (t, J=8.4 Hz, 2H), 1.13 (t, J=7.2 Hz, 3H).

16. Synthesis of 4-(3-(methyl(phenyl)amino)propyl) thio)phenol (16)

A mixture of compound 9a (250 mg, 11 mmol) and 4-mercaptophenol (140 mg, 1.1 mmol) in ACN (10 mL) was stirred at 50° C. with argon for 3 hours. DIPEA (0.23 mls, 1.1 mmol) was added to the mixture and the reaction was stirred overnight. The solvent was evaporated and the residue was purified by silica gel column chromatography with 16% yield as a pale oil, compound 16 (48 mg, 0.18 mmol). HRMS (ESI, positive) m/z calcd. for C16H20NOS [M+H]+: 274.12601, found: 274.12601. $^1$H NMR (400 MHz, Chloroform-d) δ 7.38-7.26 (m, 4H), 6.80 (m, 5H), 3.49 (t, J=7.2 Hz, 2H), 2.96 (s, 3H), 2.90 (t, J=7.0 Hz, 2H), 1.91 (p, J=7.1 Hz, 2H).

17. Synthesis of 2-(ethyl(phenyl)amino)-N-(4-hydroxyphenyl)acetamide (17)

Synthesis of 2-chloro-N-(4-hydroxyphenyl)acetamide (17a)

To a solution of 4-aminophenol (1.0 g, 9.1 mmol) in CH$_3$COOH (3.5 mL) and saturated CH$_3$COONa (3.5 mL), chloroacetylchloride (0.72 mL, 9.1 mmol) was added dropwise. After the addition was complete, the mixture was stirred at room temperature for 3 hours. The reaction mixture was concentrated, washed with water (3×25 mL) and dried over vacuum to isolate the intermediate 17a as white solid (0.690 g, 3.71 mmol, 40% yield). $^1$H NMR (DMSO, 400 MHz) δ 10.03 (s, 1H), 9.27 (s, 1H), 7.36 (d, J=8.8 Hz, 2H), 6.71 (d, J=8.8 Hz, 2H) 4.182 (s, 2H).

Synthesis of 2-(ethyl(phenyl)amino)-N-(4-hydroxyphenyl)acetamide (17)

To a solution of compound 17a (250 mg, 1.35 mmol) and N-ethylaniline (0.326 mg, 2.69 mmol) in acetonitrile (6.0 mL) was added diisopropylethylamine (0.55 mL, 4.04 mmol) dropwise. After the addition was complete, the reaction was stirred at 60° C. for 12 hours. The reaction mixture was concentrated and purified by column chromatography to isolate the compound 17 as a colorless oil (150 mg, 0.55 mmol 41% yield). MS (ESI, positive) m/z calcd. for C16H19N2O2 [M+H]+: 271.14, found: 270.95. $^1$H NMR (CDCl$_3$, 400 MHz) δ 8.34 (s, 1H), 7.27-7.31 (m, 4H), 6.88 (t, J=7.2 Hz, 1H), 6.80 (t, J=8.4 Hz, 4H), 3.96 (s, 2H), 3.53 (q, J$_1$=J$_2$=7.2, 2H), 2.20 (s, 1H), 1.24 (t, J=6.8 Hz, 3H).

18. Synthesis of 3-(2-(ethyl(phenyl)amino)ethoxy)phenol (18)

A mixture of compound 3a (500 mg, 2.7 mmol), K$_2$CO$_3$ (750 mg, 5.4 mmol), KI (90 mg, 0.54 mmol) in DMF (50 mL) was bubbled with argon for 10 min Resorcinol (600 mg, 5.4 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water and then brine and dried over $Na_2SO_4$. The solvent was evaporated and the residue was purified by silica gel column chromatography with $CH_2Cl_2$ to provide the compound 18 (380 mg, 1.48 mmol, 55%) as a light-yellow oil. $^1H$ NMR (DMSO-d6, 400 MHz) δ 9.38 (s, 1H), 7.15 (t, J=8 Hz, 2H), 7.04 (t, J=8 Hz, 1H), 6.70 (d, J=8 Hz, 2H), 6.57 (t, J=7.2 Hz, 1H), 6.32 (m, 3H), 4.02 (t, J=5.8 Hz, 2H), 3.64 (t, J=5.8 Hz, 2H), 3.44 (q, J=7 Hz, 2H), 1.10 (t, J=7 Hz, 3H); $^{13}C$ NMR (CDCl$_3$, 100 MHz): δ 155.14, 151.95, 142.80, 125.44, 124.66, 111.56, 107.52, 103.46, 102.10, 97.43, 60.60, 44.77, 40.83, 7.34; HRMS (ESI, positive) m/z calcd. for C16H20NO2 [M+H]+: 258.1494, found: 258.1534.

19. Synthesis of 2-(2-(ethyl(phenyl)amino)ethoxy)phenol (19)

A mixture of compound 3a (500 mg, 2.7 mmol), $K_2CO_3$ (750 mg, 5.4 mmol), KI (90 mg, 0.54 mmol) in DMF (50 mL) was bubbled with argon for 10 min Catechol (600 mg, 5.4 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water and then brine and dried over $Na_2SO_4$. The solvent was evaporated and the residue was purified by silica gel column chromatography with $CH_2Cl_2$ to provide the compound 19 (400 mg, 1.55 mmol, 57%) as a white solid. $^1H$ NMR (DMSO-d6, 400 MHz) δ 8.86 (s, 1H), 7.15 (t, J=8 Hz, 2H), 6.90 (d, J=8 Hz, 1H), 6.78 (m, 5H), 6.57 (t, J=7.2 Hz, 1H), 4.07 (t, J=6.0 Hz, 2H), 3.68 (t, J=6.0 Hz, 2H), 3.45 (q, J=6.8 Hz, 2H), 1.10 (t, J=6.8 Hz, 3H); $^{13}C$ NMR (CDCl$_3$, 100 MHz): δ 148.00, 146.35, 145.81, 129.47, 122.24, 120.06, 117.24, 115.04, 112.86, 67.44, 49.79, 45.65, 12.19; HRMS (ESI, positive) m/z calcd. for C16H20NO2 [M+H]+: 258.1494, found: 258.1465; calcd. for C16H19NO2Na [M+Na]+: 280.1313, found: 280.1345.

20. Synthesis of N-(2-(4-aminophenoxy)ethyl)-N-ethylaniline (20)

Compound 21 (100 mg, 0.36 mmol) was dissolved in 10 mL methanol. 50 mL of concentrated HCl was added and the reaction was refluxed for 3 hrs. The reaction mixture was concentrated, neutralized with sat. $K_2CO_3$, and extracted with EtOAc (2×25 mL), washed with water and then brine and dried over $Na_2SO_4$. The solvent was evaporated and the residue was purified by silica gel column chromatography provide the compound 20 (90 mg, 0.35 mmol, 97% yield) as a brown oil. $^1H$ NMR (CDCl$_3$, 400 MHz) δ 7.24 (t, 2H), 6.73 (m, 7H), 4.07 (t, 2H), 3.49 (q, 2H), 1.21 (t, J=7.2 Hz, 3H); HRMS (ESI, positive) m/z calcd. for C16H21N2O [M+H]+: 257.1654, found: 257.1756.

21. Synthesis of N-(4-(2-(ethyl(phenyl)amino)ethoxy)phenyl)acetamide (21)

Compound 3a (590 mg, 3.2 mmol), $K_2CO_3$ (887 mg, 6.4 mmol), KI (106 mg, 0.66 mmol) were mixed in DMF (50 mL). 4-aminophenol (600 mg, 5.4 mmol) was added portionwise, the reaction mixture was heated and stirred at 80° C. for 18 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water and then brine and dried over $Na_2SO_4$. The solvent was evaporated and the residue was purified by silica gel column chromatography provide the compound 21 (570 mg, 1.9 mmol, 60% yield) as a pale solid. $^1H$ NMR (CDCl$_3$, 400 MHz) δ 7.39 (d, J=9.2 Hz, 2H), 7.26 (t, J=7.6 Hz, 2H), 6.68-6.87 (m, 5H), 4.10 (t, J=6.0 Hz, 2H), 3.72 (t, J=6.4 Hz, 2H), 3.49 (q, J=7.2 Hz, 2H), 2.16 (s, 3H), 1.21 (t, J=7.2 Hz, 3H); HRMS (ESI, positive) m/z calcd. for C18H23N2O2 [M+H]+: 299.17540, found: 299.17538.

22. Synthesis of N-ethyl-N-(2-(4-(piperidin-1-yl)phenoxy)ethyl)aniline (22)

Compound 20 (120 mg, 0.47 mmol) and glutaraldehyde (46 mg, 0.23 mmol) was dissolved in 10 mL 1,2-dichloroethane and sodium triacetoxyborohydride (400 mg, 1.89 mmol) was added portionwise over 6 hrs and reaction was stirred overnight. The reaction was quenched with sat. sodium carbonate, extracted with EtOAc (2×25 mL), washed with water and then brine and dried over $Na_2SO_4$. The solvent was evaporated and the residue was purified by silica gel column chromatography provide the compound 22 (55 mg, 0.17 mmol, 36% yield). $^1H$ NMR (CDCl$_3$, 400 MHz) δ 7.23-7.28 (m, 2H), 6.68-6.94 (m, 7H), 4.10 (t, J=6.4 Hz, 2H), 3.72 (t, J=6.4 Hz, 2H), 3.50 (q, J=7.2 Hz, 2H), 3.05 (t, J=5.6 Hz, 4H), 1.72-1.78 (m, 4H), 1.54-1.60 (m, 2H), 1.22 (t, J=6.8 Hz, 3H); HRMS (ESI, positive) m/z calcd. for C21H29N2O [M+H]+: 325.2280, found: 325.2227.

23. Synthesis of N-methyl-N-(3-phenoxypropyl)aniline (23)

Synthesis of N-(3-bromopropyl)-N-methylaniline (23a)

N-methylaniline (1.01 mL, 9.33 mmol) was reacted with 1,3-dibromopropane (0.947 mL, 9.33 mmol) and diisopropylethylamine (2.55 mL, 18.66 mmol) in ACN at 70° C. for 12 hours. The solvent was evaporated and the residue was purified by silica gel column chromatography to provide the intermediate 23a as a yellow oil (0.80 g, 3.52 mmol, 37% yield). HRMS (ESI, positive) m/z calcd. for $C_{10}H_{15}NBr$ [M+H]+: 228.03824, found: 228.03824. $^1H$ NMR (CDCl$_3$, 400 MHz) δ 7.67 (t, J=8.4 Hz, 2H), 6.71 (d, J=8.0 Hz, 2H), 6.617 (t, J=7.2 Hz, 1H), 3.562 (t, J=6.8 Hz, 2H), 3.431 (t, J=7.2 Hz, 2H), 2.878 (s, 3H), 2.072 (m, 2H).

Synthesis of N-methyl-N-(3-phenoxypropyl)aniline (23)

To a solution of 23a (0.20 g, 0.88 mmol) and phenol (0.75 g, 0.79 mmol) in DMF (5.0 mL) was added $K_2CO_3$ (0.24 g, 1.75 mmol). The reaction was then stirred at 80° C. for 12 hours. The reaction mixture was concentrated and purified by column chromatography to isolate the compound 23 as a colorless oil (0.12 g, 0.49 mmol, 56.7% yield). MS (ESI, positive) m/z calcd. for C16H20NO [M+H]+: 242.15, found: 241.93. $^1H$ NMR (CDCl$_3$, 400 MHz) δ7.22-7.33 (m, 4H), 6.92-6.99 (m, 3H), 6.69-6.77 (m, 3H), 4.04 (t, J=6.0 Hz, 2H), 3.58 (t, J=6.8 Hz, 2H), 2.97 (s, 3H), 2.06-2.12 (m, 2H).

24. Synthesis of N-ethyl-N-(2-(4-methoxyphenoxy)ethyl)aniline (24)

To a mixture of 3 (78 mg, 0.3 mmol), $K_2CO_3$ (95 mg, 0.69 mmol), in acetone (50 mL), 1 mL (16 mmol) of MeI was added. The reaction mixture was heated to reflux for 48 hr. After cooling to room temperature, the solvent was evaporated and the residue was quenched with 50 mL water. The mixture was then extracted with EtOAc and the combined organic layer was washed with water, then brine, and dried over $Na_2SO_4$. The solvent was evaporated and the residue was purified by silica gel column chromatography with hexane/$CH_2Cl_2$ (2/1) to provide compound 24 (49 mg, 0.18 mmol, 60% yield) as a yellow oil. $^1$H NMR (CDCl$_3$, 400 MHz) δ 7.23 (m, 2H), 6.83 (m, 4H), 6.73 (d, J=8.4 Hz, 2H), 6.68 (t, J=7 Hz, 1H), 4.07 (t, J=6.4 Hz, 2H), 3.77 (s, 3H), 3.70 (t, J=6.4 Hz, 2H), 3.47 (q, J=7 Hz, 2H), 1.20 (t, J=7 Hz, 3H); $^{13}$C NMR (CDCl$_3$, 100 MHz): δ 153.93, 152.91, 147.62, 129.38, 115.95, 115.40, 114.67, 111.80, 66.01, 55.74, 49.76, 45.59, 12.30; HRMS (ESI, positive) m/z calcd. For C17H22NO2 [M+H]+: 272.1645, found: 272.1646.

25. Synthesis of 4,4'-(2,2'-(phenylazanediyl)bis(ethane-2,1-diyl)bis(oxy))diphenol (25)

A mixture of N,N-bis(2-chloroethyl)aniline (500 mg, 2.29 mmol), $K_2CO_3$ (634 mg, 4.59 mmol), and KI (76 mg, 0.46 mmol) in DMF (50 mL) was bubbled with argon for 10 min Hydroquinone (1.32 g, 12 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water, then brine, and dried over $Na_2SO_4$. The solvent was evaporated and the residue was purified by silica gel column chromatography to provide compound 25 (150 mg, 0.41 mmol, 18% yield) as a yellow oil. $^1$H NMR (DMSO-d6, 400 MHz) δ 8.91 (s, 2H), 7.16 (t, J=7.8 Hz, 2H), 6.78-6.72 (m, 6H), 6.66-6.60 (m, 5H), 4.02 (t, J=5.8 Hz, 2H), 3.75 (t, J=5.8 Hz, 2H); $^{13}$C NMR (CDCl$_3$, 100 MHz): δ 152.87, 149.60, 147.31, 129.50, 116.55, 116.08, 115.56, 111.79, 65.91, 50.99; HRMS (ESI, positive) m/z calcd. for C22H24NO4 [M+H]+: 366.1700, found: 366.1701.

26. Synthesis of 4,4'-((((4-methoxyphenyl)azanediyl)bis(ethane-2,1-diyl))bis(oxy))diphenol (26)

Synthesis of N,N-bis(2-chloroethyl)-4-methoxyaniline (26a)

4-methoxyaniline (1.0 g, 8.13 mmol) was refluxed with 1-bromo-2-chloroethane (3.5 ml, 40 mmol) and N,N-diisopropylethylamine (2.6 ml, 15 mmol) in acetonitrile (50 mls) for 24 hours at 72° C. The solvent was evaporated and the residue was purified by silica gel column chromatography to provide the intermediate 26a (100 mg, 5% yield) as a yellow oil. $^1$H NMR (CDCl$_3$, 400 MHz) δ 6.85-6.88 (m, 2H), 6.72 (d, J=8.8 Hz, 2H), 3.78 (s, 3H), 3.59-3.71 (m, 8H).

Synthesis of 4,4'-((((4-methoxyphenyl)azanediyl)bis(ethane-2,1-diyl))bis(oxy))diphenol (26)

A mixture of compound 26a (100 mg, 0.6 mmol), $K_2CO_3$ (110 mg, 0.8 mmol), and KI (15 mg, 0.02 mmol) in DMF (50 mL) was bubbled with argon for 10 min. Hydroquinone (220 mg, 2 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water, then brine, and dried over $Na_2SO_4$. The solvent was evaporated and the residue was purified by silica gel column chromatography with hexane/EtOAc (3:1) to provide the compound 26 (20 mg, 0.05 mmol, 13% yield). $^1$H NMR (CDCl$_3$, 400 MHz) δ 6.82-6.87 (m, 2H), 6.72-6.78 (m, 10H), 4.90 (bs, 2H), 4.07 (t, J=6.0 Hz, 4H), 3.76 (t, J=8.0 Hz, 7H).

27. Synthesis of methyl 4-(4-(bis(2-(4-hydroxyphenoxy)ethyl)amino)phenyl)butanoate (27)

Synthesis of methyl 4-(4-(bis(2-chloroethyl)amino)phenyl)butanoate (27a)

A mixture of chlorambucil (600 mg, 2 mmol), HBTO (625 mg, 2 mmol), and N,N-diisopropylethylamine (300 uL, 2 mmol) was stirred in methanol at 55° C. for 18 hrs. After cooling to room temperature, the solvent was evaporated and the residue was quenched with 50 mL water. The mixture was then extracted with EtOAc and the combined organic layer was washed with water, then brine, and dried over $Na_2SO_4$. The solvent was evaporated and the residue was purified by silica gel column chromatography with hexane/$CH_2Cl_2$ (10:1) to provide the compound 27a (350 mg, 1.1 mmol, 55% yield) as a yellow oil. $^1$H NMR (400 MHz, Chloroform-d) δ 7.20-7.05 (dd, 2H), 6.71-6.62 (dd, 2H), 3.75-3.70 (m, 4H), 3.69 (s, 3H), 3.64 (m, 4H), 2.58 (t, J=7.6 Hz, 2H), 2.35 (t, J=7.5 Hz, 2H), 1.93 (p, J=7.6 Hz, 2H). HRMS (ESI, positive) m/z calcd. for C15H22Cl2NO2 [M+H]+: 318.10221, found: 318.10216.

Synthesis of methyl 4-(4-(bis(2-(4-hydroxyphenoxy)ethyl)amino)phenyl)butanoate (27)

A mixture of compound 27a (470 mg, 1.48 mmol), $K_2CO_3$ (440 mg, 3 mmol), and KI (50 mg, 0.3 mmol) in DMF (50 mL) was bubbled with argon for 10 min. Hydroquinone (660 mg, 6 mmol) was added to the mixture under argon. The reaction mixture was heated and stirred at 80° C. for 6 hr. After cooling to room temperature, the solvent was evaporated and the residue was quenched with 100 mL water. The mixture was adjusted pH to ~7 with diluted hydrochloric acid. The mixture was then extracted with EtOAc and the combined organic layer was washed with water, then brine, and dried over $Na_2SO_4$. The solvent was evaporated and the residue was purified by silica gel column chromatography to provide the compound 27 (150 mg, 0.32 mmol, 22% yield) as a brown oil. $^1$H NMR (CDCl$_3$, 400 MHz) δ 7.05 (d, J=8.4 Hz, 2H), 6.67-6.81 (m, 9H), 5.58 (bs, 2H), 4.09 (t, J=6.4 Hz, 4H), 3.80 (t, J=6.0 Hz, 7H), 3.69 (s, 3H), 2.56 (t, J=7.2 Hz, 2H), 2.35 (t, J=7.2 Hz, 2H), 1.89-1.96 (m, 2H); HRMS (ESI, positive) m/z calcd. for C27H32NO6 [M+H]+: 466.2230, found: 466.2204.

28. Synthesis of 4-(4-(bis(2-(4-hydroxyphenoxy)ethyl)amino)phenyl)butanoic acid (28)

Compound 27 (60 mg, 0.13 mmol) was refluxed in concentrated hydrochloric acid for 2 hours. The reaction was concentrated, quenched with 50 mL of water, and neutralized with ammonium hydroxide to pH 7. The mixture was then extracted with EtOAc and the combined organic layer was washed with water, then brine, and dried over $Na_2SO_4$. The solvent was evaporated to yield the compound 28 (50 mg, 0.11 mmol, 85% yield). $^1$H NMR ($CDCl_3$, 400 MHz) δ 12.00 (bs, 1H), 8.92 (bs, 2H), 6.98 (d, J=8.0 Hz, 2H), 6.66-6.77 (m, 10H), 3.99-5.05 (m, 4H), 3.72 (t, J=5.6 Hz, 4H), 2.44 (t, J=7.2 Hz, 2H), 2.17 (t, J=7.2 Hz, 2H), 1.72 (q, J=7.2, 7.6 Hz, 2H); HRMS (ESI, positive) m/z calcd. for C26H30NO6 [M+H]+: 452.2073, found: 452.2007.

29. Synthesis of (((phenylazanediyl)bis(ethane-2,1-diyl))bis(oxy))bis(4,1-phenylene) diacetate (29)

Compound 25 (66 mg, 0.18 mmol) was added to a flask with acetic anhydride (72 mg, 0.72 mmol), dichloromethane (10 mls), and pyridine (cat). The reaction was stirred at room temperature for four hours, then the solvent was evaporated and the residue was purified by silica gel column chromatography to provide the compound 29 (67 mg, 0.15 mmol, 85% yield). $^1$H NMR ($CDCl_3$, 400 MHz) δ 7.26 (m, 2H), 6.99 (dd, 4H), 6.87 (dd, 4H), 6.77 (m, 3H), 4.16 (t, J=5.8 Hz, 4H), 3.88 (t, J=6.2 Hz, 4H), 2.29 (s, 6H); HRMS calculated for C26H28NO6 [M+H]: 490.19111 Observed: 490.19124.

Example 3

Structure-Function Analysis of ROS-Activated Compounds

The general structure of the ROS-activated compounds disclosed herein was probed to determine how positions in the structure alter potency in aqueous media. Compounds were screened against HeLa cells to determine $IC_{50}$ values. Cell viability was monitored by an MTT dye that forms a purple formazan product in viable cells that are undergoing metabolism. Concentrations of test compounds ranged from 0 to 100 µM and $IC_{50}$ values were calculated using a four parameter regression analysis of at least three replicates. Errors reported are between two separate experiments; independent curve-fitting had r greater than 0.95). $IC_{50}$ values for cell viability are set forth in Table 1 above.

Compound 3 represents the starting point for structure-function analysis. Compound 1, an aniline derivative that lacks an N-alkyl group, exhibited a modest reduction in cytotoxicity compared to compound 3. Potency was restored when the compound possessed an N-methylamine moiety, as evidenced by compound 2.

Replacement of the methyl group of compound 2 with a more bulky isopropyl group at the aniline nitrogen, as in compound 4, resulted in a decrease in potency relative to compound 2. When a second reactive hydroquinone moiety was added to the other alkyl position, as in compound 25, potency doubled relative to compound 3.

Referring to Formulas I and II, compounds 1-8 demonstrate the changes in potency observed when different $R_1$ and $R_2$ groups are present, with results indicating the presence of an amine group is beneficial for compound potency.

The effect of the carbon chain between the amine and the hydroquinone ether was also probed. Compounds 2, 9, 11, and 13 vary with respect to n; compounds 3, 10, 12, and 14 similarly vary with respect to n, with a different $R_2$. Results indicate that a carbon linker of 2-6 carbons provides suitable compounds.

When considering the aniline ring system, it was found that conversion to a benzylamine, as in compound 8, slightly decreased potency. Conversion of the aniline amine to an amide, as in compound 17, decreased potency. Complete removal of the aniline resulted in a loss of potency, indicating the presence of the amine, together with its $R_1$ and $R_2$ substituents, is required for activity. Loss of potency was also observed when the terminal phenol was removed (compare to compound 9), as in compound 23. Loss of potency was also observed in a compound lacking the hydroquinone moiety entirely. Compounds 15-17 demonstrate the effect of varying Q in Formula II, namely, that alkyl phenyl ethers, alkyl phenyl thioethers, and acetanilide can be tolerated at the Q position.

The relative position of $R_3$ was examined in compounds 3, 18, and 19. Results indicate the structure can tolerate ortho, meta, and para $R_3$ substituents. In a specific embodiment, $R_3$ is a para substituent.

Results for compounds 11-12 demonstrate the benefit of an ether moiety in the instantly disclosed compounds.

Results for compounds 20-24 demonstrate that $R_3$ is amenable to substitution. In a specific embodiment, $R_3$ is phenol.

As evidenced by compound 29, groups that can be cleaved intracellularly can be tolerated in the structure with little effect.

Results for compounds 25-28 demonstrate that two rings can be tethered together with a variety of substitutions.

Figure 4:
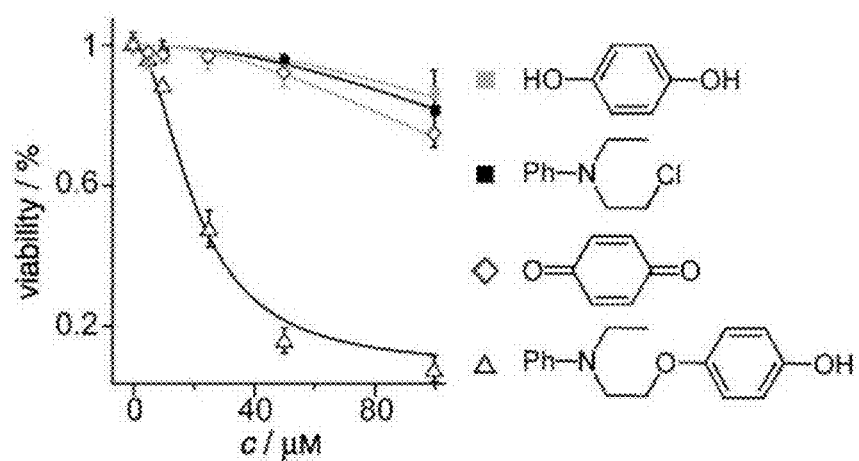
FIG. 4 shows a comparison of cellular toxicity in HeLa cells across various structural analogs. Hydroquinone (grey square) and the corresponding oxidized form, benzoquinone (open diamond), were slightly toxic with $IC_{50}$ values of 161 and 227 µM, respectively. An analog that possessed a chlorine leaving group (black square) had an estimated an $IC_{50}$ value of 211 µM. The $IC_{50}$ of ROS-activated compound 3 (open triangle) was 23 µM.

Compound 3 was cytotoxic to HeLa cells with an $IC_{50}$ of 23±5 µM (FIG. 4, triangles). In contrast, the unmodified nitrogen mustard with a chlorine-leaving group (FIG. 4, black square) had much lower cytotoxicity; the $IC_{50}$ was 211±17 µM. Cytotoxicity was not derived from the hydroquinone portion of compound 3 or from the benzoquinone oxidation product as $IC_{50}$ values of these compounds were 161±14 µM and 227±21 µM, respectively (FIG. 4, grey square and diamond, respectively).

Results for compound 24 show that cytotoxicity is induced via oxidation and not some other enzymatic process such as hydrolysis, since both compound 24 and compound 3 would have the same tendency toward enzymatic degradation, but compound 3 shows superior anti-cancer activity.

The data taken together illustrate that the hydroquinone ether tethered to an amine an advantageous molecular structure for achieving low $IC_{50}$ values (effective anti-cancer cell activity).

Example 4

Chemical Reactivity of ROS-Activated Compounds

Figure 5:
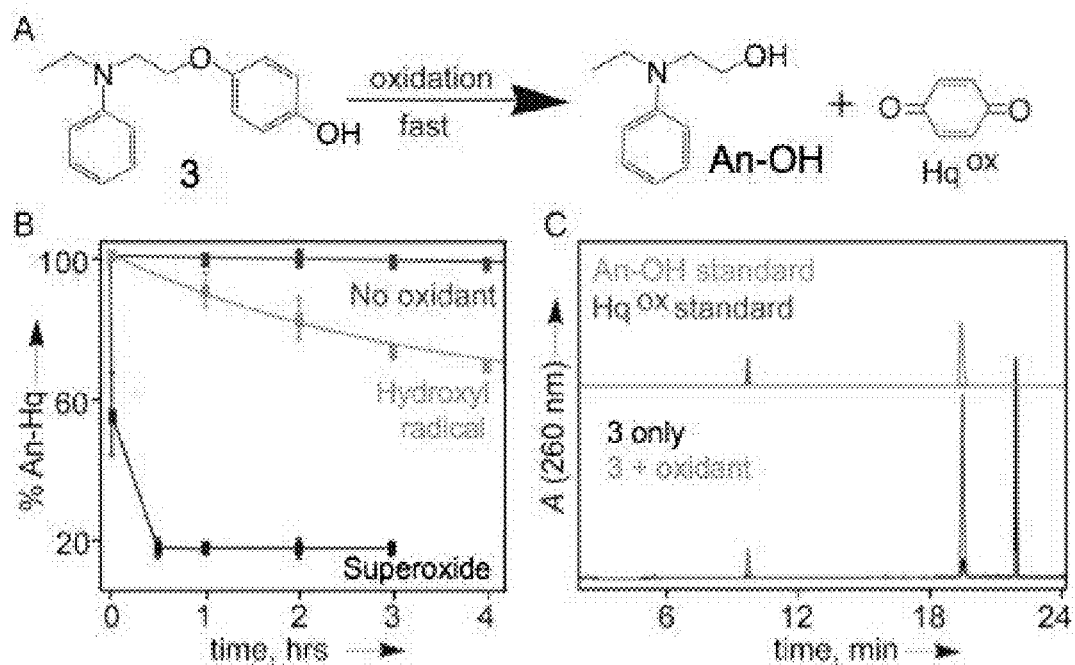
FIG. 5 demonstrates oxidation and ROS-dependent hydrolysis of compound 3 of the present invention. (A) Once oxidized by ROS, compound 3 is activated, leading to rapid reactivity and formation of benzoquinone (He) and An-OH. (B) The hydrolysis of compound 3 was monitored by HPLC at 260 nm at the indicated times. In the absence of oxidant (dark grey), compound 3 is highly stable in buffered solutions. Addition of hydroxyl radical via copper (light grey) or superoxide via oxidases (black), can also rapidly oxidize compound 3. (C) The reaction products were identified by comparison to standards. Compound 3 elutes at 22 min (black). Addition of an oxidant led to the formation of new products at 19 and 10 min (light grey). Comparison to standards of An-OH (light gray) and Hqox (dark gray) revealed that hydrolysis occurs via ejection of benzoquinone.

The oxidative and ROS-activation of the instantly disclosed compounds was investigated. Water, one of the simplest nucleophile substrates, was examined under different oxidative conditions (FIG. 5). A model ROS-activated compound, compound 3, was used to explore the chemical reactivity of these agents (FIG. 5A).

Hydrolysis of compound 3 as a function of time was quantified by separation of the reaction products by reverse-phase HPLC (FIG. 5B). In phosphate buffer, hydrolysis was slow with a half-life of 693±42 hours assuming first order kinetics. To obtain quantifiable data, time points were taken daily over one week. Results indicated that compound 3 is a poor electrophile when not oxidized or ROS-activated.

Addition of the one-electron oxidant, $Na_2Ir_2Cl_6$, led to quantitative hydrolysis of compound 3 with a half-life of 0.4±0.2 hours (FIG. 5B). The oxidation potential of Ir(IV) is 0.7 volts vs. Ag/AgCl making it an appropriate choice for oxidation of hydroquinone derivatives. In additional to oxidation, cells produce reactive oxygen species in the forms of hydroxyl radical and singlet oxygen. Copper and hydrogen peroxide can be used to produce hydroxyl radical. Oxidation of compound 3 by $CuC_{1-2}$-hydrogen peroxide led to rapid hydrolysis with a half-life of 12.1 hrs±0.7 hrs. The extent of hydrolysis was dependent on the hydrogen peroxide concentration and was slow due to lack of ascorbate (data not shown). Oxidases like horseradish peroxidase reduce molecular oxygen to either hydrogen peroxide or water and at the same time oxidize a substrate with an appropriate potential. The oxidation of compound 3 was difficult to measure via HPLC since after one minute approximately half (53±13%) of compound 3 was hydrolyzed. The hydrolysis half-life of compound 3 was increased by more 1700-fold upon addition of oxidative equivalents.

Comparison to standards characterized by reverse-phase HPLC was used to verify the hydrolysis reaction products of compound 3 (FIG. 5C). In the presence of Ir(IV), An-OH (retention time of 19 min) and benzoquinone (retention time of 10 min) were observed. An-OH is the product of hydrolysis since water has displaced the hydroquinone leaving group. Copper-hydrogen peroxide and peroxidase treatment produced the same products. These data indicate that once compounds according to Formulas I or II enter a cell, oxidases and several forms of reactive oxygen species will activate reactivity.

Example 5

NCI-60 Cell Panel Toxicity Studies

Figure 2:
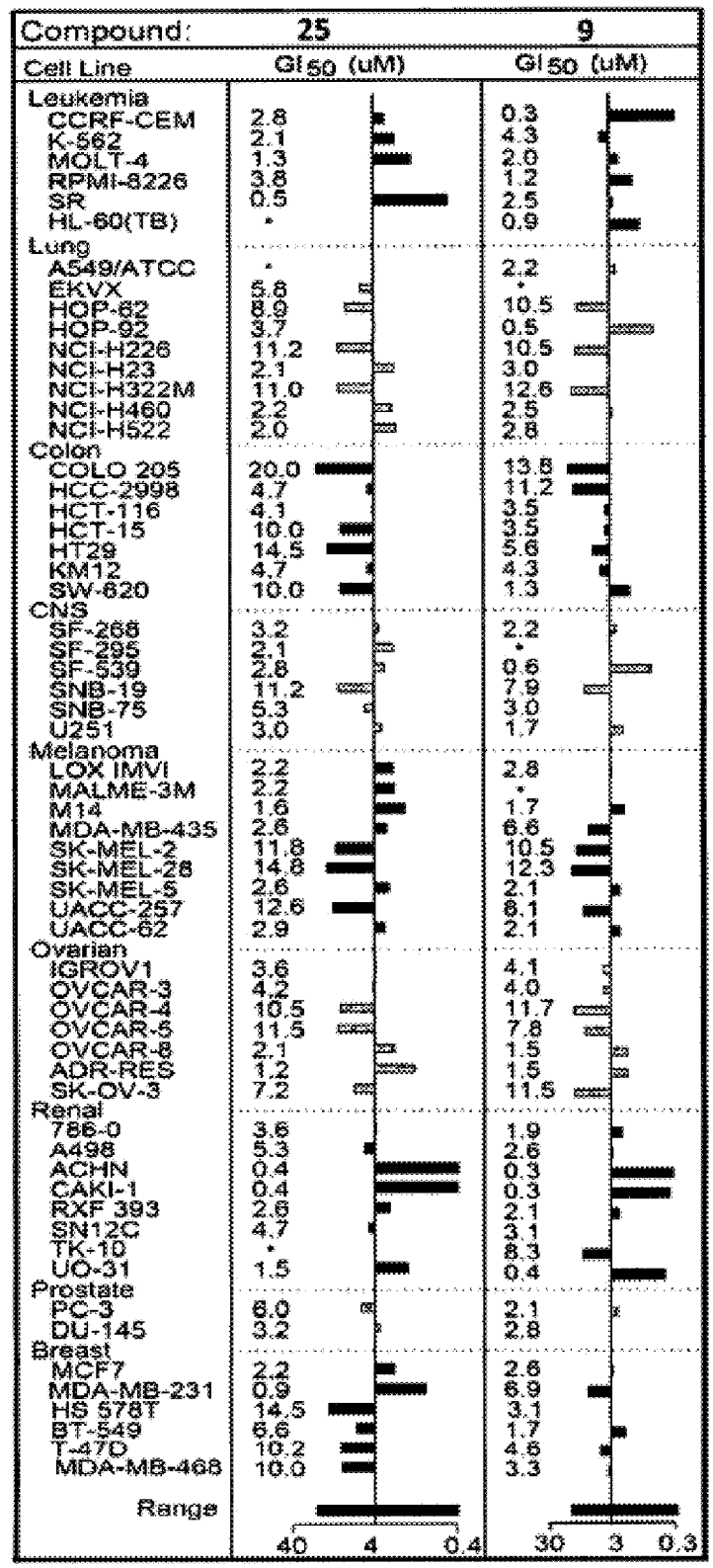
FIG. 2 shows growth inhibition ($GI_{50}$) results for compounds 9 and 25 against the NCI-60 cell panel. [*] indicates cell lines not tested.

Compounds 25 and 9 were evaluated for effects on the viability of the cell lines in the NCI-60 cell panel. Viability was monitored using a Solforhodamine B assay, which measures total protein content and is a measure of cell number rather than metabolic activity, as seen in standard MTT assays. Data is reported as growth inhibition $GI_{50}$, rather than $IC_{50}$, to reflect the change in cell counts relative to the starting number of cells. Results are shown in FIG. 2.

Compounds 25 and 9 showed selective potency against particular cell lines in the sixty-cell panel. The median $GI_{50}$ for 25 was 3.9 µM and 3.0 µM for 9 (FIG. 2) Importantly, the distribution of $GI_{50}$ values was large, with a range of 55-fold for 25 and 53-fold for 9. This data indicates that both compounds 25 and 9 demonstrate high potency against several cell types, while some cancer cells were less targeted. Growth inhibition pattern induced by 25 and 9 based on the type of cancer was also analyzed. FIG. 2 shows all $GI_{50}$ values among the various cancer types relative to the median. The majority of leukemia and renal cancer cell lines were above the median, indicating enhanced sensitivity to ROS-activating compounds. The current results further substantiate renal carcinoma as a potential target. Leukemia cells demonstrated the highest median potency, with all cell lines examined having $GI_{50}$ values below the median for 25 and five of the six below the median for 9. Compound 25 had a median $GI_{50}$ of 2.1 µM in all the leukemia cell lines tested, whereas compound 9 had a median $GI_{50}$ value of 1.9 µM. A model for acute lymphoblastic leukemia (ALL), SR-91, had $GI_{50}$ values of 470 nM for compound 25, and 2.5 µM for compound 9. Another ALL model line, CCRF-CEM, had $GI_{50}$ values of 263 nM for 9 and 2.8 µM for 25. The final ALL model line tested, MOLT-4, had $GI_{50}$ values of 2.0 µM for compound 9 and 1.3 µM for compound 25. In RPMI-8226, a plasmacytoma and myeloma cell line, 9 had a $GI_{50}$ value of 1.2 µM and 25 gave a $GI_{50}$ value of 3.8 µM. HL-60, a model of acute promyelocytic leukemia, had a $GI_{50}$ value of 900 nM for compound 9, but was not tested for compound 25. Finally, K-562, a model for myelogenous leukemia, had $GI_{50}$ values corresponding to 4.3 µM and 2.1 µM for compounds 9 and 25, respectively.

Example 6

AML Toxicity Studies

Figure 3:
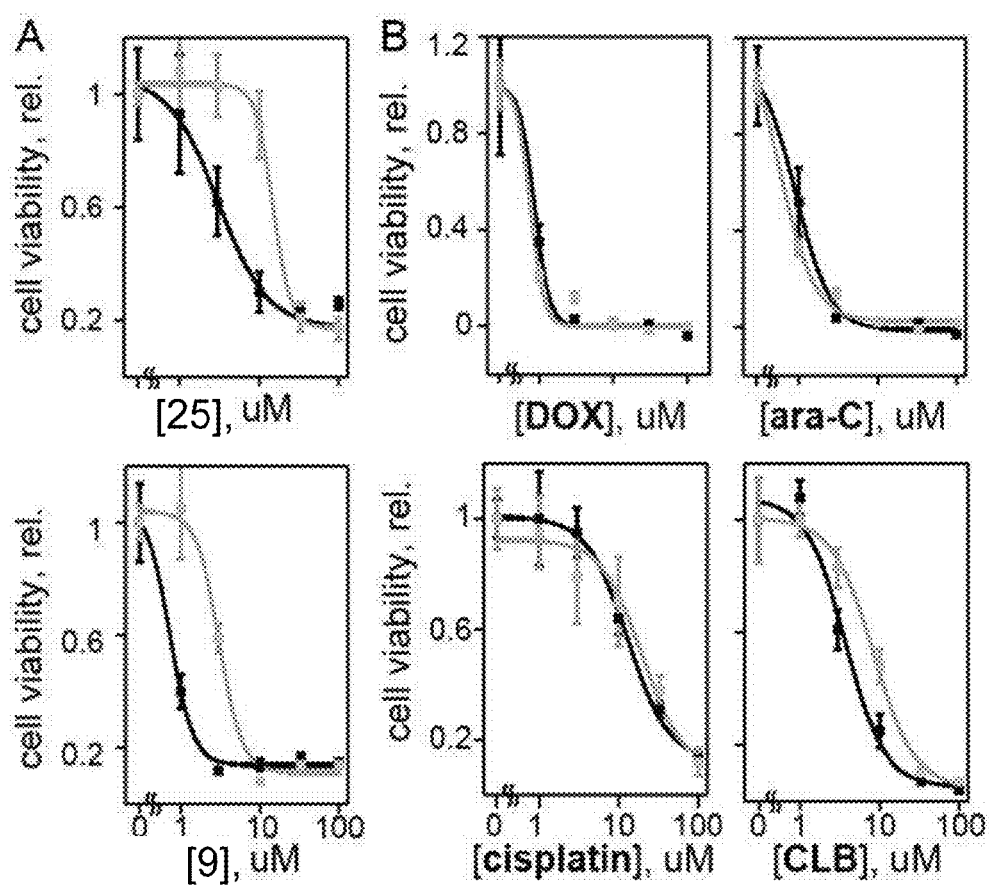
FIG. 3 shows evaluation of therapeutic indices for ROS-activated compounds and exemplary common anti-cancer agents. $IC_{50}$ values were measured in MA9.3 AML cancer cells (black lines) and human CD34+ stem/progenitor cells (grey lines). (A) shows results for ROS-activated compounds 9 and 25. (B) shows results for doxorubicin (DOX), cytosine arabinoside (ara-C), cisplatin, and chlorambucil (CLB).

To assess the anti-cancer activity against AML, transformed cells were compared to closely related, non-transformed counterparts. In the case of AML, the generally accepted non-transformed cell of origin is the human CD34+ blood stem/progenitor cell. Assessing potency against normal blood stem cells is important since, without selective cytotoxicity, an agent will yield reduced efficacy and therapeutic potential. One major limitation to current treatment is that many anti-cancer agents do not selectively inhibit growth or cause cytotoxicity to cancer cells relative to healthy cells. Therefore, a comparison of current agents and the ROS-activated compounds disclosed herein was carried out. (FIG. 3). Cytotoxicity was measured via MTT assay on CD34+ blood stem/progenitor cells (grey lines) and on the MA9.3 AML cell line (black lines), which was derived from the transformation of human CD34+ cells by introduction of the leukemia oncogene MLL-AF9.

With respect to the ROS-activated DNA-modifying compounds tested, compound 25 had an $IC_{50}$ value of 3.0±0.2 µM and 9 had an $IC_{50}$ value of 0.7±0.2 µM against MA9.3 cells. The $IC_{50}$ values against normal blood stem cells were 16±1 µM and 5.4±0.9 µM for 25 and 9, correspondingly. The therapeutic indices were 5.3±0.5 and 7.7±3 for 25 and 9, respectively. (FIG. 3A).

Therapeutic indices for known anti-cancer agents were examined (FIG. 3B). The foundations of AML treatment are the anti-cancer agents doxorubicin and ara-C. Doxorubicin and ara-C showed strong potency against MA9.3 AML cells with $IC_{50}$ values of 0.086±0.05 µM and 0.92±0.03 µM, respectively; these agents had $IC_{50}$ values against CD34+ blood stem/progenitor cells of 76±18 nM and 0.59±0.09 µM, demonstrating very limited selectivity. The therapeutic index for doxorubicin was 0.9±0.2 and the index for ara-C was 0.6±0.1. The negative index for ara-C was statistically significant but small. Thus, these two agents showed low selectivity. Other commercially available DNA-modifying agents were also analyzed for selectivity, as a base of comparison for the instantly disclosed ROS-activated DNA-modifying agents. Cisplatin was selected for its high therapeutic use and chlorambucil was selected for its utilization in chronic lymphocytic leukemia. The $IC_{50}$ value for cisplatin was 14±0.7 µM and for chlorambucil was 8.7±0.3 µM against MA9.3 AML cells. Against CD34+ blood stem/progenitor cells, the former had an $IC_{50}$ value of 15±2 µM, while the latter had an $IC_{50}$ value of 11±1 µM. The therapeutic index for cisplatin was 1.0±0.2, while the index for chlorambucil was 1.3±0.1. Chlorambucil showed slight selectivity.

Results show that ROS-activated DNA-modifying agents have favorable therapeutic indices and statistically significant selectivity against AML cancer cells.

Example 7

Renal Cancer and CNS Cancer Toxicity $IC_{50}$ values for compounds 9 and 25 were determined via a Sulforhodamine B viability assay. Results are shown in FIG. 6, with $IC_{50}$ values in the micromolar range and errors less than 25%. Results indicate compounds 9 and 25 showed efficacy against a range of renal and CNS cancer cell lines.

Example 8

DNA Modification Studies

Compound 3 and compound 25 were examined for their ability to modify DNA upon oxidative activation. As is the new convention, the numbering for 2'-deoxyguanosine (hereinafter "dG") is retained. See e.g., Cooke, M. S. et al., *Recommendations for standardized description of and nomenclature concerning oxidatively damaged nucleobases in DNA*, Chem. Res. Toxicol. 23:705-07 (2010). The numbering for the compound 3 phenol derivatives is denoted by a double prime, even when discussing the phenol without addition to dG. Based on previous examples, it was determined that the hydroquinone was the active portion of the molecule, forming a product mass corresponding to formation of a benzetheno-2'-deoxyguanosine upon addition of an oxidant in the presence of dG. Previous literature demonstrated that benzoquinone can add to 2'-deoxyguanosine and produced a 3"-hydroxy-1,N2-benzetheno-2'-deoxyguanosine, wherein the first step in the reaction mechanism was a Michael addition. See e.g., Munk, B. H., et al., *Exploration of mechanisms for the transformation of 8-hydroxy guanine radical to FAPyG by density functional theory*, Chem. Res. Toxicol. 20:432-44 (2007). Thus, the ability of compound 3 to react and form the same benzetheno-2'-deoxyguanosine adduct was investigated.

Figure 7:
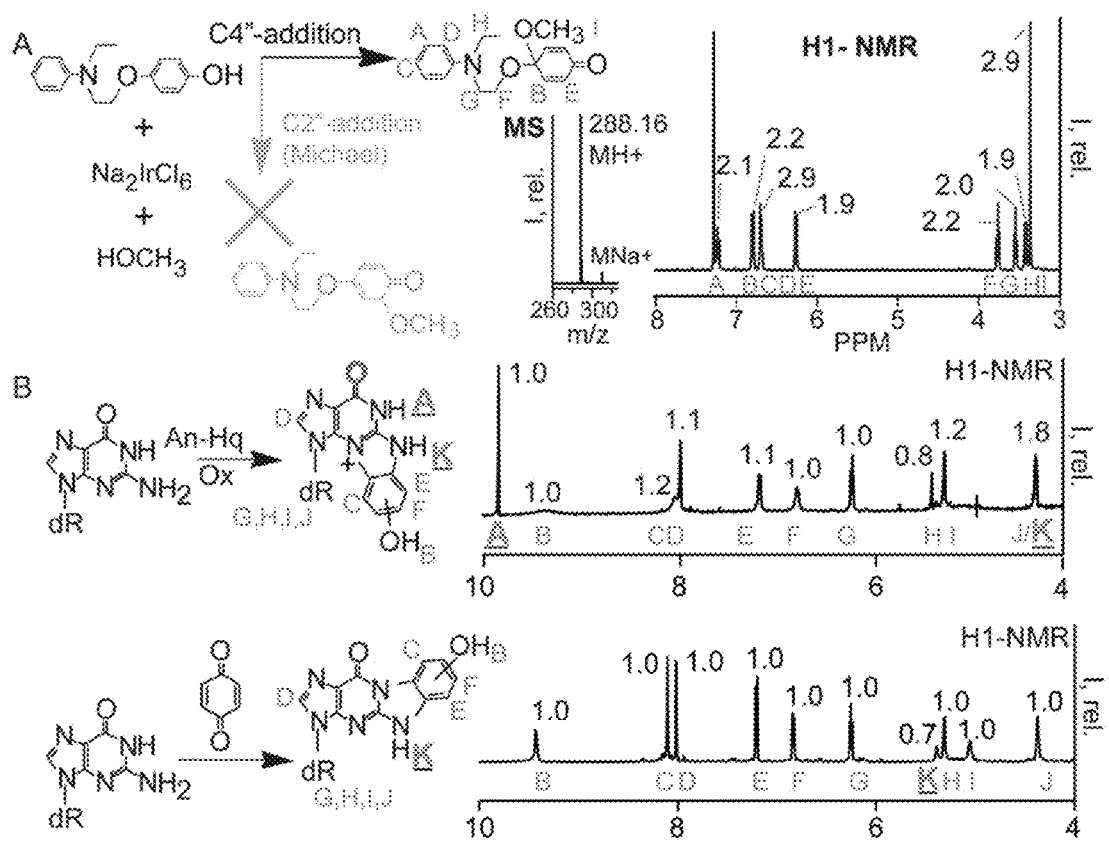
FIG. 7 shows (A) (Left) pathways and products thereof through which quinones can react (C4" addition, black, and C2"-Michael addition, grey), and (Right) NMR and MS spectra of the C4" addition product; (B) (Top Left) the reaction between 2'-deoxyguanosine, compound 3, and $Na_2IrCl_6$, (Top Right) NMR spectra of the dG-adduct formed upon reaction between 2'-deoxyguanosine, compound 3, and $Na_2IrCl_6$, (Bottom Left) the reaction between 2'-deoxyguanosine, and benzoquinone according to literature, and (Bottom Right) NMR spectra of the benzetheno-adduct formed upon reaction 2'-deoxyguanosine and benzoquinone.

Compound 3 was reacted with $Na_2IrCl_6$ in methanol to induce oxidation (FIG. 7A). Solvolysis by methanol served as a simple nucleophile and as a means to trap the site of nucleophilic addition.

More specifically, compound 3 (10 mg, 0.039 mmol) was dissolved in methanol (2 mL). $Na_2IrCl_6.6H_2O$ (43 mg, 0.078 mmol) and N,N-diisopropylethylamine (4.5 mg, 0.039 mmol) were added to the mixture. The mixture was reacted at room temperature for 0.5 hr. The reaction was filtered through silica gel and washed with acetonitrile. The filtrate was concentrated and the residue was purified by flash chromatography on silica gel to provide the product (9 mg, 0.017 mmol, 90% yield) as a yellow oil. Upon oxidation, compound 3 was 90% oxidized to a new compound after 15 min.

$^1$H-NMR was used to analyze the isolated product; $^1$H NMR (CDCl$_3$, 400 MHz) δ 7.23 (t, J=8.2 Hz, 2H), 6.80 (d, J=10.4 Hz, 2H), 6.69 (m, 3H), 6.26 (d, J=10.0 Hz, 2H), 3.76 (t, J=6.2 Hz, 2H), 3.54 (t, J=6.2 Hz, 2H), 3.41 (q, J=7.1 Hz, 2H), 3.36 (s, 3H), 0.87 (t, J=7.1 Hz, 3H); HRMS (ESI, positive) m/z calculated for C17H22NO3 [M+H]+: 288.1600, found: 288.1614. The region between 3 and 8 ppm is shown in FIG. 7A. There were eighteen protons in this region, indicating a product with an additional methoxy group. The singlet peak at 3.4 ppm with an integration of 2.9 corresponded to the added methoxy group. The aromatic region was symmetric, indicating that addition did not occur at C3" or C2" of the phenol through Michael addition.

Mass spectrometry (MS) was used to ensure a product consistent with a single methanol addition. MS was performed as follows: the isolated product was resuspended in 100 μL of 0.25% acetic acid and 15% acetonitrile. Infusion into the instrument occurred at a rate of 5 μL/min. The mass spectrometry was performed on a Thermo Fisher Scientific LTQ-FT, a hybrid instrument consisting of a linear ion trap and a Fourier transform ion cyclotron resonance mass spectrometer. The entire elutant was introduced into the LTQ-FT, using the standard electrospray ionization source for the instrument with a spray voltage of 5 kV and a capillary temperature of 275° C. Autogain control was used set to 500,000 with a maximum injection time of 1250 ms for FT-ICR full scans. Collision induced dissociation, MS/MS, was executed in the linear trap with an AGC setting of 10,000 and a maximum injection time of 500 ms. FT-ICR full scans were acquired in the positive ion mode at 100,000 resolving power at m/z 400. Results indicated that compound 3 did not behave like benzoquinone. Instead, oxidative activation led to a potent electrophile, via addition at C4". This inferred that the DNA lesion produced may be different than benzoquinone, and that these agents did not simply release benzoquinone as their mechanism of action.

Figure 8:
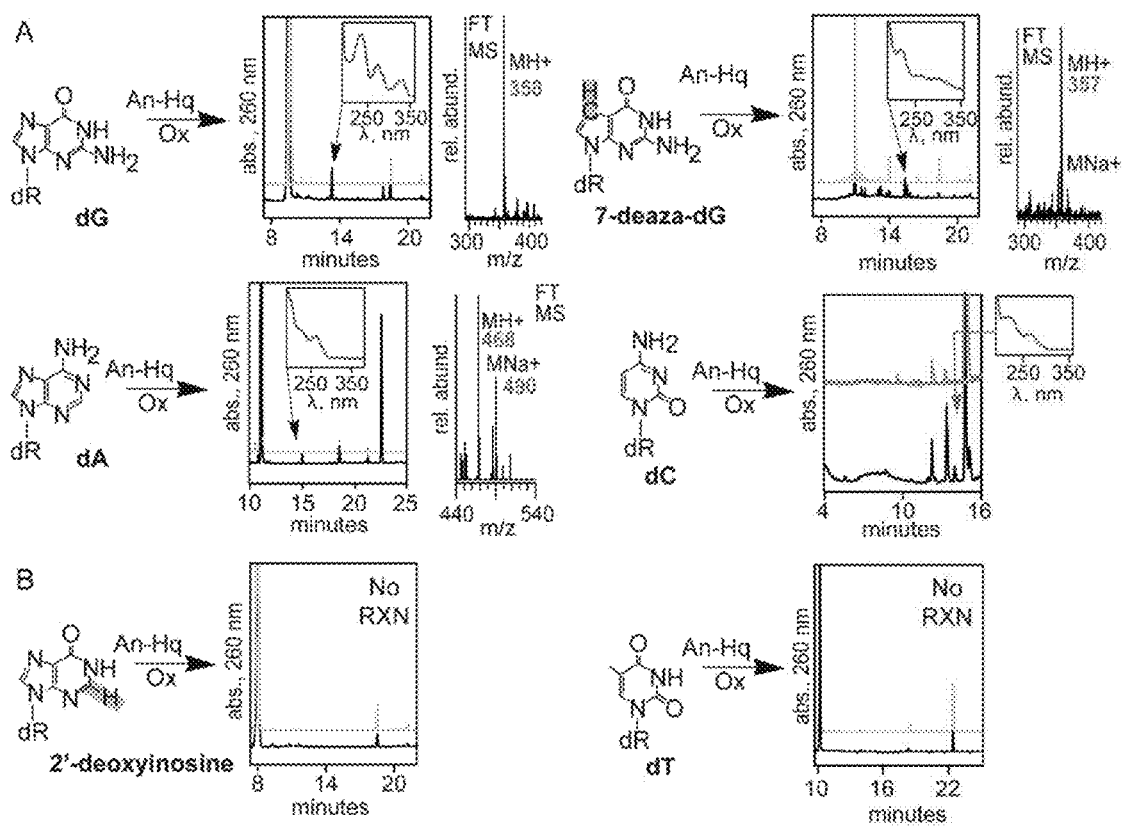
FIG. 8 shows (A) (Top) the reaction between dG or 7-deaza-dG, an oxidant, and compound 3, chromatograms of the reaction product of dG or 7-deaza-dG, an oxidant, and compound 3 (black) and of a control (grey) containing no compound 3 or oxidant, and MS spectra of the reaction product of dG or 7-deaza-dG, an oxidant, and compound 3, and (Bottom) the reaction between dA or dC, an oxidant, and compound 3, chromatograms of the reaction product of dA or dC, an oxidant, and compound 3 (black) and of a control (grey) containing no compound 3 or oxidant, and MS spectra of the reaction product of dA, an oxidant, and compound 3, and (B) the reaction between 2'-deoxyinosine or dT, an oxidant, and compound 3, chromatograms of the reaction product of 2'-deoxyinosine or dT, an oxidant, and compound 3 (black) and of a control (grey) containing no compound 3 or oxidant.

As there was a difference in reactivity due to oxidative activation, the produced lesion was investigated through NMR analysis (FIG. 7B). For consistency, the NMR was labeled starting from A for both products. The DNA lesion formed upon incubation of compound 3 was compared to that formed with benzoquinone. The product of compound 3, $Na_2IrCl_6$, and dG in water-phosphate buffer was used to isolate the dG-adduct formed. Specifically, compound 3 (22 μl dissolved in DMSO, 1 mmol) was added to phosphate buffer (2 mL, 25 mM $NaH_2PO_4$ in 5% acetonitrile and 95% $H_2O$, pH 8.0) which contained 0.4 mmol of dG. $Na_2Ir_2Cl_6$ (22 μl dissolved in water, 1 mmol) was added, and the reaction was mixed. The oxidant used was $Na_2IrCl_6$ because it possessed the correct potential to oxidize the agents but not dG. See e.g., Munk, B. H. et al., *Exploration of mechanisms for the transformation of 8-hydroxy guanine radical to FAPyG by density functional theory*, Chem. Res. Toxicol. 20:432-44 (2007). The reaction of benzoquinone and dG was established by Jowa et al. as well as by Chema and Singer. See e.g., Chenna, A. et al., *Synthesis of a benzene metabolite adduct, 3"-Hydroxy-1,N2-benzetheno-2'-deoxyguanosine, and Its site-specific incorporation into DNA oligonucleotides*, Chem. Res. Toxicol. 10:165-171 (1997); and Jowa, L. et al., *Synthesis and characterization of deoxyguanosine-benzoquinone adducts*, J. Appl. Toxicol. 10:47-54 (1990). Accordingly, dG was incubated in dimethylformamide (hereinafter "DMF") and potassium carbonate. This non-aqueous system formed the known benzetheno-adduct in high yield. After reaction, the products were purified to greater than 95% purity levels (data not shown). Analysis by positive ion MS showed products with an m/z value of 358.1146 and an elemental composition of $C_{16}H_{16}N_5O_5^+$ (FIG. 8). MS/MS showed deglycosylation, indicating that the ribose portion of the nucleoside was not modified (data not shown).

$^1$H NMR experiments were carried out on a Bruker DGX-501, 500 MHz instrument. Chemical resonances are reported in δ (ppm) units, using residual $^1$H signals from deuterated solvents as references. The reaction listed was scaled to 100-fold (total volume 200 mL). The reaction was incubated in the dark at 25° C. for four days. Solvent was evaporated and the adduct of interest was purified in two stages. First, a Biotage SP1 Flash system, outfitted with a 5.5 g RediSep Rf Gold C18 column, was used to purify the reaction mixture, using a 97% water and 3% methanol buffer A and methanol for buffer B. The gradient was 0% methanol to 10% over 10 column volumes, 10% to 100% over 3 column volumes and held there for 5 column volumes. The sample (~75% pure by HPLC) was collected after 13 column volumes and was lyophilized to remove solvent. The second stage employed HPLC purification, using a Grace Alltima HP C8 semi-preparative column (3 μm, 7×53 mm) at 2.5 ml/min. Solvent A was 95% water and 5% acetonitrile and solvent B was 95% acetonitrile and 5% water. The gradient was 0% B for 5 min, 30% B over 8 min, 100% B over 3 min and then held there for 4 min Absorbance was monitored at 260 nM. The collected sample eluted around 8 min. After HPLC purification, the product was dried and dissolved into 500 μL d6-DMSO and evaluated by NMR for 15 hrs to determine the $^1$H-NMR.

Reaction of benzoquinone revealed addition at N1,N2 as had been previously observed (FIG. 7B, bottom). Ten resonances between the 4-10 ppm were shown. The B shift was a singlet at 9.4 ppm and was ascribed to the terminal phenol hydrogen at C1". Two strong singlets, C and D, were observed at 8.0. These singlets were the C8-hydrogen and the C2"-hydrogens, with the C2" being more deshielded. Importantly, the C8-hydrogen indicated that the five-membered ring of guanine was not modified. Accordingly, without being bound by the theory, it is believed that N7 was not the addition site. Resonances E and F were the remaining C5" and C6" singlet phenol hydrogens. Taken together, the three phenol resonances indicated two dG positions have added to the phenol. The triplet at 6.2 ppm, G, is the C3'-hydrogen. The resonances H, I, and J were all ribose protons, both hydroxyl and ribose. Finally, shift K is the hydrogen at N2. This hydrogen was found to be easily exchangeable and, hence, its integration was low. A drop of D$_2$O was added to differentiate exchangeable and non-exchangeable protons (data not shown). Resonances B, H, I, and K were found to be exchangeable further confirming our NMR assignments.

Analysis of the compound 3-dG adduct was accomplished in a similar manner (FIG. 7B, top). Again, ten resonances were observed with some key differences. Several resonances were identical to the 3"-hydroxy-1,N2-benzetheno-2'-deoxyguanosine adduct. Shift D, the C8-hydrogen, confirmed that compound 3 did not modify N7 on the five-membered ring. Likewise, resonances B, G, H, I, and J directly overlapped (compare FIG. 7B top and bottom) indicating modification was not at the ribose. The NMR identified several distinct hydrogens. Two new hydrogen peaks were seen. First, the A shift at 9.9 ppm was a strong singlet. Without being bound by the theory, it is believed that such a strongly deshielded hydrogen could only come from the amido-hydrogen at N1. In addition, the K-shift at the N2 hydrogen was observed at 4.3 ppm. Importantly, shift A (bolded in FIG. 7B) indicated that the N1 position was no longer part of the phenol-dG adduct. This was interesting because, if taken with the appearance of the C8-hydrogen, the NMR revealed that the phenol added to N2 and N3.

To further support the data that compound 3 is producing a different hydroxy-benzetheno-2'-deoxyguanosine adduct, stability in acid was determined (data not shown). It has been observed that N2,3-benzetheno-2'-deoxyguanosine adducts are prone to degradation by incubation in acid since a weaker glycosidic bond is present. See e.g., Khazanchi, R. et al., *N-2,3-Etheno-2"-deoxyguanosine [8,9-dihydro-9-oxo-2-"deoxy-3-beta-D-ribofuranosylimidazo[2,1-B]purine]—a practical synthesis and characterization*, J. Org. Chem. 58:2552-56 (1993). Incubation at pH 1 and elevated temperatures led to degradation of the adduct when compared to the 3"-hydroxy-1,N2-benzetheno adducts (data not shown). It should be noted that several tautomers can be drawn that assign correctly to the NMR data (not shown) Importantly, this data showed that compound 3 generated a distinct lesion from benzoquinone, stemming from the oxidative activation mechanism of compound 3.

A series of HPLC analyses to determine which DNA bases were modified by compound 3 were performed (FIG. 8). Nucleosides were incubated with compound 3 and Na$_2$IrCl$_6$. More specifically, compound 3 (22 μl dissolved in DMSO, 1 mmol) was added to phosphate buffer (2 mL, 25 mM NaH$_2$PO$_4$ in 5% acetonitrile and 95% H$_2$O, pH 8.0) which contained 0.4 mmol of the listed nucleoside. Na$_2$Ir$_2$Cl$_6$ (22 μl dissolved in water, 1 mmol) was added, and the reaction was mixed.

After the incubation period, reactions were analyzed by HPLC with UV detection set to 260 nm. More specifically, product was monitored using a Beckman Coulter System Gold HPLC equipped with a diode array detector (260 nm detection) for lesion formation twice a day for 7 days. HPLC conditions were as follows: a Cosmosil 5C18-PAQ Waters column was used (4.6ID, 150 mm in length). The gradient (solvent A=95% water, 5% acetonitrile and solvent B=5% water, 95% acetonitrile) was linear: 0% B for 5 min, 100% B over 20 min, 100% B for 4 min, 0% B over 2 min and held for 4 min For each nucleoside, a reaction chromatogram (black) and control chromatograms (grey) are shown. Each of the controls excludes a single reaction component: compound 3, dG, and Na$_2$IrCl$_6$. The reaction of dG with compound 3 is shown on the top left of FIG. 8. A clearly observable product was seen at 13 min when comparing the controls and reaction traces. The product had a characteristic three band absorbance spectrum (inset). Mass Spectrometry analysis showed a predominate ion at m/z of 358, and the elemental composition is $C_{16}H_{16}N_5O_5^+$ with less than 300 ppb error. For MS, peaks were collected, dried to remove solvent (if stable, if not they were directly injected into MS), and then analyzed by MS. All yields were between 0.5 and 3%, depending on the nucleoside adduct. It should be noted that there was a small product at 18 min which possessed an m/z value equal to the deglycosylation product (data not shown).

To the top right in FIG. 8, 7-deaza-dG was also examined for reactivity. The NMR revealed that N7 was not involved in the reaction. Based on this data, without being bound by the theory, it is believed that substitution of dG with 7-deaza-dG should not interfere with formation of reaction product. By performing the same reaction with 7-deaza-dG, a new series of products were observed at 15 min. Again, these products had similar UV absorbance. The MS spectra had a mass change of 1 amu or $C_{17}H_{17}N_4O_5^+$, which is correct for a 7-deaza-dG adduct with an added phenol. This data indicated that N7 is not involved in the reaction. To further validate the NMR results, 2'-deoxyinosine was reacted with compound 3 (FIG. 8B, bottom left). 2'-deoxyinosine lacks N2 and, according to the NMR results, should not react. The reaction was prepared identically to the reaction with dG. No product formation was observed, further confirming the NMR results that N2 is required for product formation.

Compound 3 adduct formation was observed with each nucleoside. Analysis of the reaction between 2'-deoxyadenosine and compound 3 revealed a new product at 15 min (FIG. 8, middle left). The absorbance was similar with the dG adduct formed. The product was formed in low yield. The yield was ~0.4%. The MS analysis for this adduct gave a mass indicative that two phenols had added (addition of 188 amu). Addition of two phenols has been observed in the literature involving quinone addition to nucleosides. See e.g., Jowa et al. The reaction with 2'-deoxycytidine (FIG. 8, middle right) gave even less product, which limited characterization to HPLC. Finally, no adduct formation was observed upon incubation with thymidine (FIG. 8, bottom right). Without being bound by the theory, it is believed that the key difference is that thymidine lacks a nucleoside aryl amine. Altogether, this data demonstrated that the oxidative activation of compound 3 and its derivatives generated an electrophile that can add to exocyclic amino groups of adenine, guanine, and cytosine. Without being bound by the theory, it is believed that the yield of these reactions on double stranded DNA will differ from nucleosides as the aryl amines of adenine and cytosine are accessible from the major groove, while N2 of guanine is accessible from the minor groove.

Figure 9:
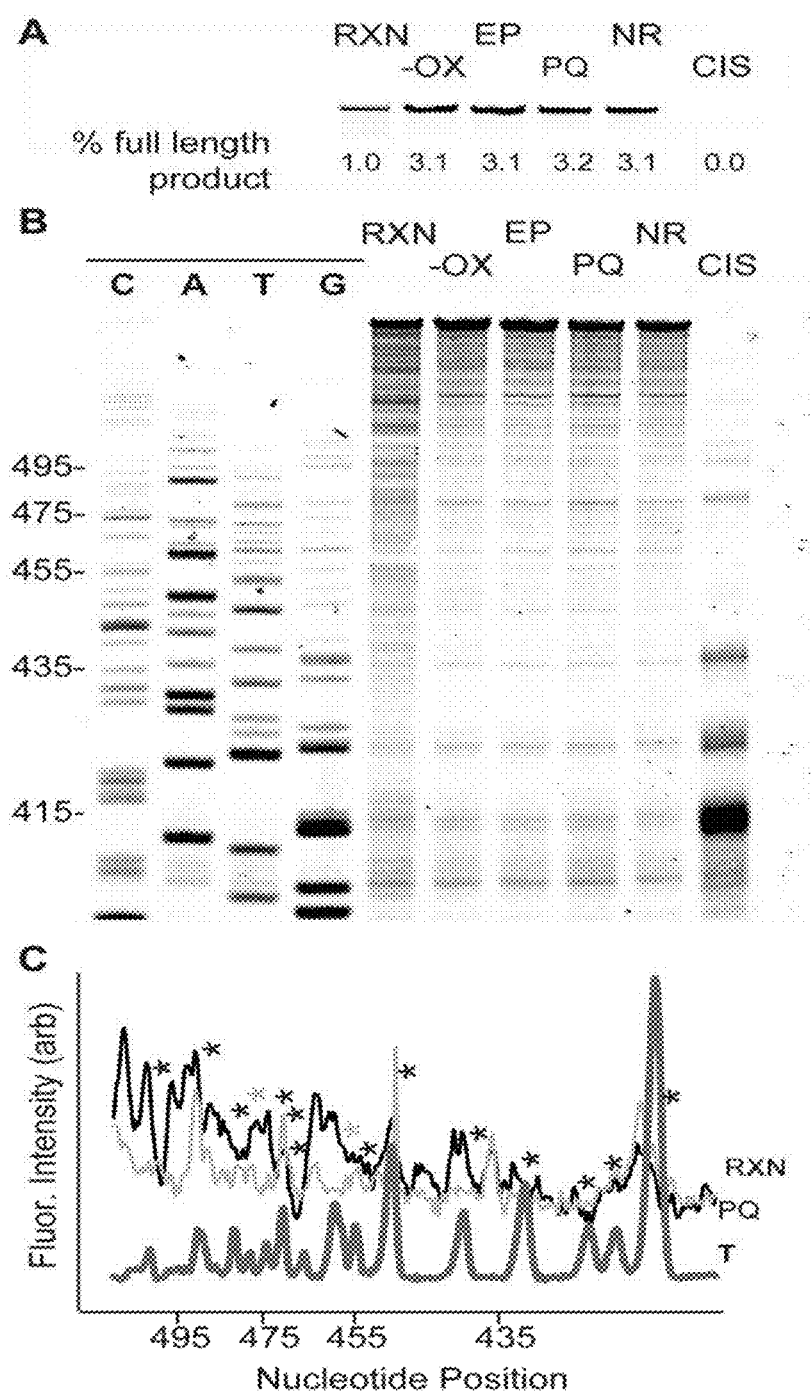
FIG. 9 shows (A) full-length extension product upon primer extension from a 392-nucleotide dsDNA in control lanes and loss of full-length extension product upon primer extension from a 392-nucleotide dsDNA following incubation with either cisplatin (CIS) or compound 25 (RXN) in the presence of an oxidant; (B) sequence dependent damage with sequence lanes on the left, wherein DNA incubated with compound 25 and oxidant (RXN) caused damage at most sequences; and (C) quantification of compound 25 damage (RXN), wherein extension stops in the reaction (black) and in the pre-quenched control (light grey) were compared to a thymine sequence lane (T, dark grey).

With the ability to modify three out of the four nucleosides through different parts of the helix, the agents' reactivity with double stranded DNA (dsDNA) was investigated, a biologically relevant substrate. Reaction of compound 25, i.e., An-Hq$_2$, with Na$_2$IrCl$_6$ and a large DNA strand would enable identification of specific DNA base sequences susceptible to damage by the agents (FIG. 9). A 392-nucleotide section of the pUC19 plasmid, positions 287-678, was amplified by PCR. More specifically, primer extension experiments were performed using a 392-nucleotide dsDNA, synthesized from pUC19 plasmid vector (New England Biolabs). A 30 cycle PCR amplification (55° C. for 30 s, 75° C. for 45 s, and 95° C. for 30 s) was performed, using a 19-nucleotide forward primer, GGCCTCTTCGCTATTACGC (SEQ ID NO:1), starting at the nucleotide at position 287 of the vector, and an 18-nucleotide reverse primer, ATACGCAAACCGCCTCTC (SEQ ID NO:2), starting at position 672. See e.g., Solivio, M. J. et al., *Copper generated reactive oxygen leads to formation of lysine-DNA adducts*, J. Inorg. Biochem. 104:1000-05 (2010). The oligonucleotide was purified using a Cycle Pure Kit (Omega BioTek, Norcross, Ga.), yielding a final concentration of 40 μg/μL. DNA was reacted with the agent, compound 25, and Na$_2$IrCl$_6$ for 5 hrs at 37° C. (720 μg DNA, 0.2 mM sodium phosphate, pH=8, 0.5 mM compound 25, and 2 mM iridium). For the pre-quenched control, DNA was added 24 hrs after the agent and the oxidant were mixed. The end products were benzoquinone and N-phenyldiethanolamine. Each sample of reacted DNA was then added to the primer extension mix (1× vent buffer, 100 μM dNTP, 200 nM primer, 0.05 U/μL vent(exo-) DNA polymerase). The primer was fluorescently-labeled with IRDye700. The fluorescently labeled primer used overlaps at positions 370-389. Twelve cycles were accomplished (55° C. for 15 s, 72° C. for 1 min, and 95° C. for 30 s). Denaturing load dye was then added to the samples, and a 12% denaturing PAGE gel was performed. The gel was visualized using the Odyssey Infrared Imaging System (LiCor) with 169 μm resolution and the 700-channel. Sequencing was performed by standard methods, using manual sequencing of the 392-nucleotide PCR product and acyclo-terminators, except the fluorescently labeled M13 primer was substituted. Experiments were performed in triplicate, and standard errors were calculated.

The nucleotides listed in FIG. 9 sequence lanes corresponded to the template strand. For example, bands in the G lane are equivalent to the G nucleotides in the 392-nucleotide template. Agent and oxidant were required to stop primer extension. When the unmodified DNA was extended, a full-length PCR product of 301 by was observed. Comparison of the unreacted primer and full-length product allowed calculation of percent yield of the primer extension (FIG. 9A). Several controls were utilized to identify unique damage produced by the activated compound 25. The controls included a minus Na$_2$IrCl$_6$ control (i.e., —OX), the end products produced after compound 25 oxidation (i.e., EP), a pre-quenched reaction control (i.e., PQ), and a negative control containing only DMSO (i.e., NR). Each control yielded 3.1-3.2% full-length product and demonstrated that oxidative activation was required. The end products gave by compound 25 oxidation produced a 3.1±0.4% extension yield, similar to the minus oxidant control. This control established that the end products did not cause extension stops in high yield. When the 392-nucleotide DNA was incubated with already oxidized compound 25, a similar yield of 3.2±0.1% full-length extension product was observed. The no reagent control yielded a 3.1±0.1% extension yield. As a positive control, the 392-nucleotide DNA was incubated with cisplatin, a known DNA modifying agent which induces replication stops at DNA damage sites. As expected, no full-length extension product was observed in the cisplatin positive control. Next, compound 25 was tested to further investigate its DNA modifying capabilities. Treatment of the 392-nucleotide DNA with compound 25 followed by oxidative activation led to a reduction in the full-length product from 3.2% to 1.0±0.2%, or a decrease of 69±0.6%. Without being bound by the theory, it is believed that the decline in product formation showed that compound 25 and its derivatives modified dsDNA and stopped the progression of the DNA polymerase in vitro.

The primer extension assay provided further evidence that damage induced by compound 25 and its derivatives is not only guanine specific (FIG. 9B). The positive control, cisplatin, reacted at guanine repeats. This can be seen in the CIS lane of the gel, where the largest replication stop was at position 413. The corresponding sequence is 5'-GGGG. The negative controls (i.e., —OX, EP, PQ, and NR) had limited replication stops. These stops were attributed to the polymerase's inability to pass certain structural features on the hard to replicate cloning region of pUC19. In contrast, activated compound 25 in the RXN lane was capable of modifying bases at most positions. When looking at positions 410-470, most nucleotides showed a greater than two-fold enhancement in the early terminations. In particular, guanine at positions 412-414, 422-423, and 430-436 all exhibited replication stops. Stops at adenine also occurred. For example, replication stops were observed at 410 and 430. Similar extension stops at cytosine positions 415-419 and 440-441 were observed. There were few predominate stops in the extension, with 76% of all three of these base types showing an increase in extension stops between two and four fold. In contrast, little modification at thymine was observed. The thymine positions on the 392-nucleotide sequence are denoted by asterisks in FIG. 9C. The sequence 5'-TT at position 421 and 422 displayed limited extension stops when compared to the pre-quench control. Several other thymine residues showed no change in extension stops. In fact, only two thymine nucleotides out of nineteen had any difference between the PQ and RXN (FIG. 9C, grey asterisks). Without being bound by the theory, this data illustrated that compound 25 and its derivatives can modify DNA in vitro, and that modification occurs at several types of DNA bases. This data is in-line with the nucleoside reactivity studies shown in FIG. 8.

Reactivity with DNA was further explored in vitro using a 12-nucleotide oligonucleotide. The sequence chosen was a self-complementary sequence of 5'-GCGCAATTGCGC-3' (SEQ ID NO:3), which had a molecular weight of 3646 g/mol with an elemental composition of $C_{116}H_{147}N_{46}O_{70}P_{11}$. It is believed that reaction with compound 25 will produce addition of one benzetheno-group to the oligonucleotide that would increase the molecular weight to 3736 g/mol with an elemental composition of $C_{112}H_{149}N_{46}O_{71}P_{11}$. This difference is quite large and is readily detected via FT-MS. The oligonucleotide was annealed to form dsDNA, reacted with compound 25 and an oxidant, and incubated for three days. More specifically, the DNA was annealed in 25 mM sodium phosphate. Prior to reaction, the DNA was desalted and placed in 5 mM Ammonium Acetate buffer, pH 8.0. The 100 μL reaction contained 2 mM DNA, 10 mM compound 25, and 10 mM of a (diacetoxyiodo)benzene oxidant. The reaction was left at room temperature in the dark for three days.

Figure 10:
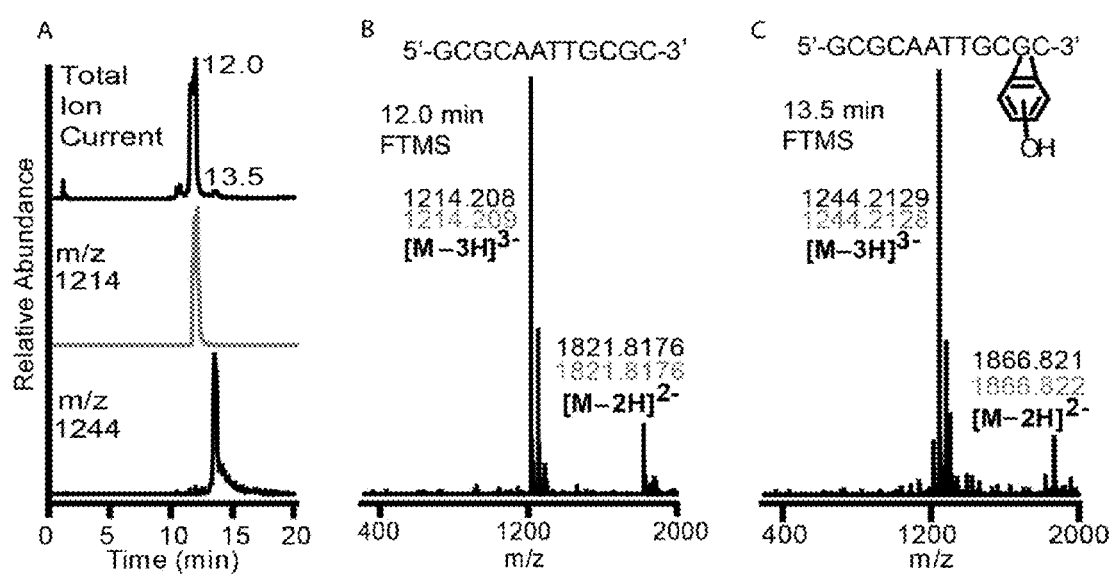
FIG. 10 shows (A) LC/MS of the product of the reaction of compound 25 with an oligonucleotide, 5'-GCGCAAT-TGCGC (SEQ ID NO: 3), in the presence of an oxidant, wherein (Top) is a total ion current, (Middle) is an ion chromatogram for 1214 m/z (grey), and (Bottom) is an ion chromatogram for 1244 m/z (black); (B) FT-MS spectra at 12.0 min showing unmodified DNA with a mass of 1214.208 for the triply charged and 1821.8176 for the doubly charged unmodified oligonucleotide, wherein (Top) is the sequence of the DNA; and (C) FT-MS spectra at 13.5 min showing a modified DNA with masses of 1244.2129 for the triply charged and 1866.821 for the doubly charged state, wherein (Top) is the sequence of the DNA with a modified guanine, and wherein experimental masses are indicated in black and theoretical masses are indicated in grey.

The reaction mixture was then analyzed by LC/MS to determine whether compound 25 formed the benzetheno-adduct on a double stranded DNA in vitro (FIG. 10). Analysis by MS utilized a Thermo Scientific LTQ-FT, a hybrid instrument consisting of a linear ion trap and a Fourier transform ion cyclotron resonance mass spectrometer. The injection volume was 10 µL. Liquid chromatography was accomplished using a Waters Symmetry C18 5 µm, 2.1×150 m column, Finnigan Surveyor MS pump, and Finnigan Micro AS autosampler. The flow rate was 200 µL/min and the gradient ranged from 2% (v/v) acetonitrile in 5 mM ammonium formate to 15% over 35 min. Autogain control was used and set at 500,000 with a maximum injection time of 1250 ms for FT-ICR full scans. FT-ICR full scans were acquired in the negative ion mode at 100,000 resolving power at m/z 400. Mass accuracy errors were below 500 ppb for full scan.

The total ion chromatogram can be seen at the top of FIG. 10A, with a predominate ion peak at 12.0 min and another ion peak at 13.5 min. The MS spectrum of the 12.0 min peak is shown in FIG. 10B. The 12.0 min spectrum has a large ion current with an m/z of 1214, which is the triply negatively charged unmodified oligonucleotide (FIG. 10B). Also observed was the doubly negatively charged ion of the unmodified oligonucleotide with an m/z value of 1821. The MS spectrum of the 13.5 min peak is shown in FIG. 10C. The major ion observed on the total ion current at 13.5 min corresponded to a m/z value of 1244, which is the expected m/z for the triply negatively charged benzetheno-oligonucleotide. Also observed was the doubly negatively charged modified oligonucleotide with an m/z of 1866. The elemental composition was determined to be $C_{122}H_{149}N_{46}O_{71}P_{11}$ with an error or 447 ppb (data not shown). The only other major ion observed in the 13.5 min FT-MS was an ion pair of the triply negatively charged oligonucleotide with trifluoroacetic acid (TFA) which has an m/z value of 1282; the TFA ion pair with the unmodified oligonucleotide was also seen in the 12.0 min FT-MS at m/z 1252. It should be noted that the modification could be at many of the nucleotide positions on the dsDNA, since modification at any location would give the same mass. This result is significant as it indicates that compound 25 can add to dsDNA and form a lesion of the same mass shown in the nucleoside studies.

Example 9

Genetic Knockdown of Nucleotide Excision Repair

Modification of DNA by compound 3 and compound 25 and repair of DNA were studied in the *Drosophila* model by a pathway involving Ercc1. A targeted transgenic RNAi knockdown experiment was conducted using the GAL4/UAS system in which expression of Ercc1 was silenced. More specifically, *Drosophila* were maintained on standard cornmeal, agar, and molasses media at 25° C. under a 12:12 hr light:dark cycle. To induce targeted gene silencing, the following RNAi line was obtained from the Vienna *Drosophila* RNAi Center: UAS-Ercc1$^{RNAi}$ (v12622$^{VDRC}$). This line was crossed to the daughterless-GAL4 (da-GAL4) driver line in order to ubiquitously inactivate gene expression. The isogenic host strain, w$^{1118}$ (60100$^{VDRC}$), was crossed to da-GAL4 as a control for genetic background effects.

Silencing of Ercc1 expression was confirmed under the da-GAL4 driver using RT-PCR (FIG. 11A). More specifically, for each sample, fifteen adult male *Drosophila* were homogenized, and total RNA was isolated using Trizol (Invitrogen, Carlsbad, Calif.). Total RNA was then DNase treated using DNA-free (Ambion, Austin, Tex.), according to manufacturer's instructions. Total RNA (0.5 µg) was reverse transcribed using the Accuscript High Fidelity First Strand cDNA synthesis kit (Agilent Technologies, Santa Clara, Calif.), and the resulting cDNA was used in RT-PCR assays. Primers were as follows: Ercc1-F 5'-CGTGCTGTACCTCTCGC-3' (SEQ ID NO: 4) and Ercc1-R 5'-CTGAGGAACGGTTC-CTG-3' (SEQ ID NO:5). Quantum RNA β-actin Internal Standards (Ambion, Austin, Tex.) were used to amplify β-actin (control) according to manufacturer's instructions, following optimization of the β-actin:competimer ratio. PCR products were separated electrophoretically on a 2% agarose gel and visualized with ethidium bromide. RT-PCR assays on two independent RNA isolations per genotype were performed.

Because of the rapid induction of these agents' mechanisms of action, the tolerated doses of these agents in *Drosophila* were monitored over the course of 7 days. To do so, differences in survival relative to the control were recorded, following delivery of compound 3 or vehicle control. See e.g., Dietzl, G., Chen, D., Schnorrer, F., Su, K.-C., Barinova, Y., Fellner, M., Gasser, B., Kinsey, K., Oppel, S., Scheiblauer, S., Couto, A., Marra, V., Keleman, K., and Dickson, B. J. (2007) A genome-wide transgenic RNAi library for conditional gene inactivation in *Drosophila*. *Nature* 448, 151-156. In the majority of injections with healthy animals with the vehicle alone, death was noted in approximately 20%. This was attributed to the stress of the injection process and was expected.

Because of the bulky lesion produced upon DNA modification, it is unlikely that *Drosophila* lacking Ercc1 expression would be able to repair the damage. Therefore, it was expected that these flies would exhibit great sensitivity toward compound 3. Microinjections were performed on individual adult male *Drosophila* between three and seven days old. Individuals were held in position for microinjection using a gentle vacuum. A thin pulled glass micropipette attached to a Picospritzer III (Parker Hannifin, Cleveland, Ohio) was used to deliver anti-cancer agents into the fly abdomen. A 0.5 µL volume of agent was injected at ~40 psi of compressed air. Agents were dissolved in 100% DMSO, and solutions were made fresh daily. Blue food dye (0.125 mg/mL) was added to the solutions to confirm the delivery of the agent. Agents tested included compound 3 and compound 25. Microinjections of the vehicle alone (control) were also performed. For each agent, ten individuals of each genotype were injected at a 10 mM concentration. A concentration of 10 mM was used because preliminary analysis showed this to be effective at eliciting a response. Post injection, flies were placed on fresh standard *Drosophila* media at 25° C. and on a 12:12 hr light:dark cycle. Individuals were scored for survival after one day and followed for a total of 7 days to examine longer-term effects of the agents. To analyze the significance of the data, chi-squared was calculated.

Figure 11:
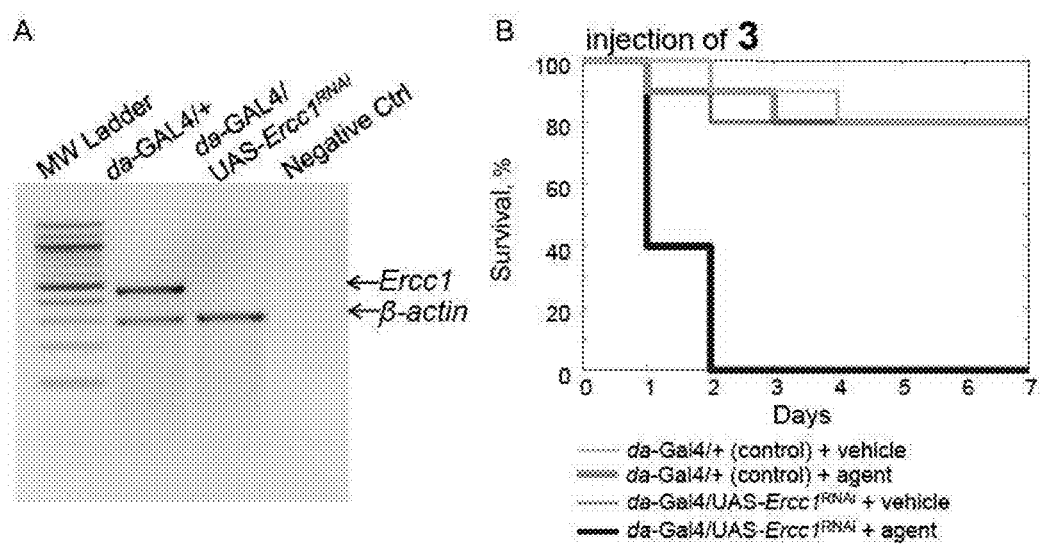
FIG. 11 shows (A) an agarose gel showing the silencing of Ecrr1 relative to beta-actin after RNAi knowdown; and (B) a graph of days with respect to survival (%) of *D. melanogaster* in which Ercc1 expression was silenced (da-GAL4/UAS-Ercc1RNAi) and *D. melanogaster* with wild-type Ercc1 expression (da-GAL4/+) injected with compound 3 or vehicle (control).

Upon injection of compound 3, only 10% of *Drosophila* had died on Day 1 in the controls (FIG. 11). In contrast, *Drosophila* lacking Ercc1 expression showed 60% death on Day 1. This result was significant at a P<0.002 and $X^2$=5.5. *Drosophila* lacking Ercc1 expression also had a significant reduction in survival with agent delivery relative to injection with the vehicle ($X^2$=8.5 P<0.003). Results indicate that compound 3 and compound 25 induced DNA modification in vivo and strongly supported their roles as DNA damaging agents with highly selective cytotoxicity.

Example 10

Potency Against Renal Carcinoma Cells

The sensitivity of renal cancer cells to treatment with compound 25 was investigated. Compound 25 was evaluated for effects on viability using a sulforhodamine B total protein content assay at the NCI Developmental Therapeutics Program. The method uses total protein content and was developed by Monks et al., *Feasibility of a high-flux anticancer drug screen using a diverse panel of cultured human tumor cell lines, J. Natl. Cancer Inst.* 83:757-66 (1991). Briefly, cells are treated with compound 25 and then fixed to the plate surface. The number of cells is proportional to the relative amount of protein as measured by sulforhodamine B. Seven renal cancer cell lines were examined: 786-0, A498, ACHN, CAKI-1, RXF 393, SN12C, and UO-31. Data at the NCI was then fit to sigmoid and the $IC_{50}$ and fitting error determined Most renal cancer cells tested were sensitive to compound 25 with a median $IC_{50}$ value was 1.8 μM Importantly, some cell lines displayed high sensitivity since the $IC_{50}$ values in ACHN and CAKI-1 cells were 360±90 and 370±40 nM, respectively. One cell line, SN12C, displayed low potency with an $IC_{50}$ value of 21±1.2 μM. Without being bound by the theory, it is believed that cancer was targeted by oxidatively-activated agents because six of the seven renal carcinoma cell lines had $IC_{50}$ values below 5 μM.

All documents cited are incorporated herein by reference in their entirety; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A compound according to Formula I:

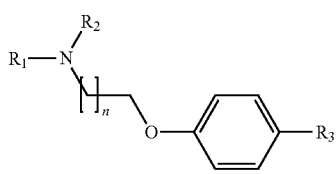

Formula I wherein:
- $R_1$ and $R_2$ are each independently selected from the group consisting of substituted or unsubstituted or branched alkyl and unsubstituted aryl wherein said alkyl and aryl optionally comprise one or more heteroatoms;
- $R_3$ is selected from the group consisting of OH, NHC(O)CH$_3$, piperidine and OC(O)CH$_3$; and n is 1-5, wherein at least one of $R_1$ and $R_2$ is aryl.

2. The compound according to claim 1, wherein alkyl substitutions are selected from the group consisting of alkoxyl, halo, OH, CN, carboxyl, carboxyl ester, and substituted or unsubstituted alkyl.

3. The compound according to claim 1, wherein $R_1$ is alkyl when $R_2$ is aryl, and wherein $R_2$ is alkyl when $R_1$ is aryl.

4. The compound according to claim 1, wherein $R_1$ and $R_2$ are each independently selected from the group consisting of substituted or unsubstituted $C_1$-$C_8$ alkyl and unsubstituted phenyl; and $R_3$ is OH.

5. The compound according to claim 1, wherein the compound is

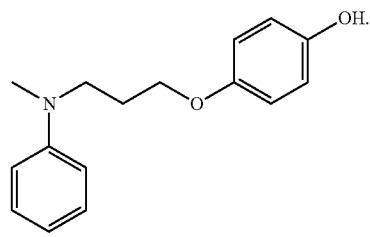 [SMILES: CN(CCCOc1ccc(O)cc1)c1ccccc1]

6. A pharmaceutical composition for the treatment of a cancer associated with elevated ROS comprising:
   (a) a therapeutically effective amount of a compound according to claim 1; and
   (b) a pharmaceutically-acceptable carrier.

7. A compound selected from the group consisting of:
   4-(2-(methyl(phenyl)amino)ethoxy)phenol;
   4-(2-(ethyl(phenyl)amino)ethoxy)phenol;
   4-(2-(isopropyl(phenyl)amino)ethoxy)phenol;
   4-(3-(methyl(phenyl)amino)propoxy)phenol;
   4-(3-(ethyl(phenyl)amino)propoxy)phenol;
   4-(4-(methyl(phenyl)amino)butoxy)phenol;
   4-(4-(ethyl(phenyl)amino)butoxy)phenol;
   4-(5-(methyl(phenyl)amino)pentyloxy)phenol;
   4-((5-(methyl(phenyl)amino)pentyl)oxy)phenol;
   4,4'-(2,2'-(phenylazanediyl)bis(ethane-2,1-diyl)bis(oxy)) diphenol; and
   (((phenylazanediyl)bis(ethane-2,1-diyl))bis(oxy))bis(4,1-phenylene) diacetate.

* * * * *